US008771700B2

(12) United States Patent
Kotenko et al.

(10) Patent No.: US 8,771,700 B2
(45) Date of Patent: Jul. 8, 2014

(54) INTERFERON ANTAGONISTS, ANTIBODIES THERETO AND ASSOCIATED METHODS OF USE

(75) Inventors: Sergei V. Kotenko, East Brunswick, NJ (US); Geoffrey L. Smith, Appleford-on-Thames (GB)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1422 days.

(21) Appl. No.: 12/310,432

(22) PCT Filed: Aug. 23, 2007

(86) PCT No.: PCT/US2007/076655
§ 371 (c)(1),
(2), (4) Date: Sep. 16, 2010

(87) PCT Pub. No.: WO2008/024919
PCT Pub. Date: Feb. 28, 2008

(65) Prior Publication Data
US 2011/0027282 A1   Feb. 3, 2011

Related U.S. Application Data

(60) Provisional application No. 60/839,499, filed on Aug. 23, 2006.

(51) Int. Cl.
*A61K 39/12* (2006.01)
*A61K 39/00* (2006.01)
*A61K 38/16* (2006.01)
*C07K 1/00* (2006.01)

(52) U.S. Cl.
USPC ............. 424/186.1; 424/192.1; 514/21.2; 530/350

(58) Field of Classification Search
None
See application file for complete search history.

(56) References Cited

U.S. PATENT DOCUMENTS 7,285,526 B2 * 10/2007 Maroun ............... 514/3.8
7,820,793 B2 * 10/2010 Kotenko et al. ........ 530/351

OTHER PUBLICATIONS

Wells, (1990), Biochemistry 29: pp. 8509-8517.*
Ngo et al., (1994), The Protein Folding Problem and Tertiary Structure Prediction, pp. 492-495.*
Hunag et al. (2007), PNAS, vol. 104, No. 23, pp. 9822-9827.*
Wilson et al. (200), J.Mol.Biol., vol. 297, pp. 237-249.*
Lee, H.J., GENBANK Accession No. AJ293568.1, Yaba-like disease virus (YLDV), complete genome (2005).
Lee et al., "The Genome Sequence of Yaba-like Disease Virus, A Yatapoxvirus" Virology 2001 281:170-192.
Search Report and Written Opinion from PCT/US07/76655, Sep. 26, 2008.

* cited by examiner

*Primary Examiner* — Christine J Saoud
*Assistant Examiner* — Jegatheesan Seharaseyon
(74) *Attorney, Agent, or Firm* — Licata & Tyrrell P.C.

(57) ABSTRACT

Described are compositions and methods useful for modulating the immune system of a subject. Also included are diagnostic methods for monitoring an immunologic condition. In particular the invention relates to antagonists of interferon proteins and associated methods of use as well as methods to develop neutralizing antibodies against IFN antagonists to treat viral infections.

7 Claims, 13 Drawing Sheets

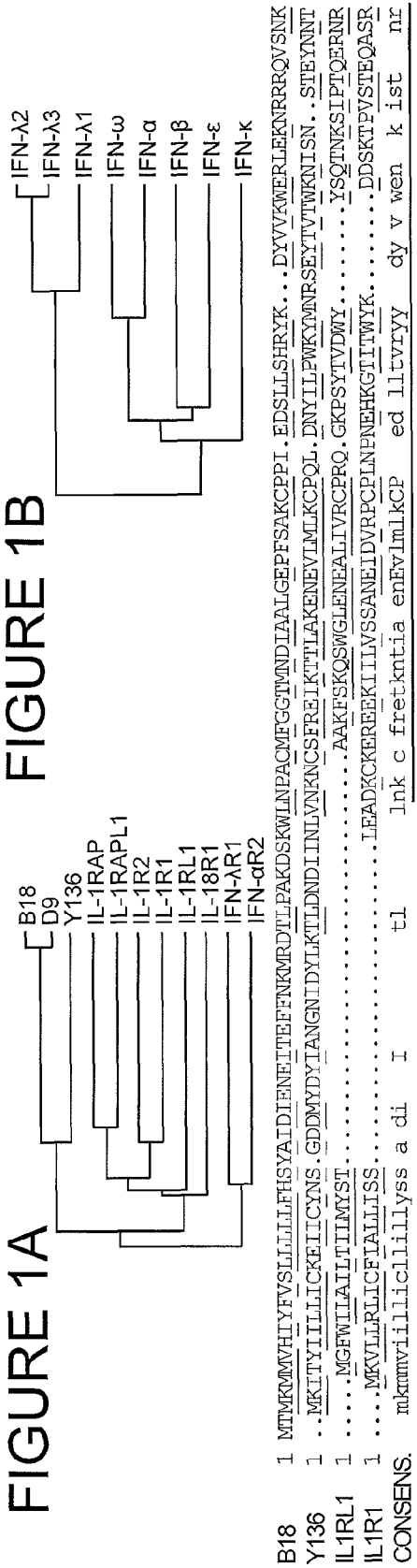

FIGURE 10A

FIGURE 10B

SEQUENCE LISTING

```
<160> NUMBER OF SEQ ID NOS: 35

<210> SEQ ID NO 1
<211> LENGTH: 351
<212> TYPE: PRT
<213> ORGANISM: yatapoxvirus
<220> FEATURE:
<221> NAME/KEY: MISC_FEATURE
<222> LOCATION: (1)..(351)
<223> OTHER INFORMATION: 136R protein (Y136) from Yaba-Like Disease
      Virus (YLDV)

<400> SEQUENCE: 1

Met Lys Ile Thr Tyr Ile Ile Leu Leu Ile Cys Lys Glu Ile Ile Cys
1               5                   10                  15

Tyr Asn Ser Gly Asp Asp Met Tyr Asp Tyr Ile Ala Asn Gly Asn Ile
            20                  25                  30
```

Asp Tyr Leu Lys Thr Ile Asp Asn Asp Ile Ile Asn Leu Val Asn Lys
         35                  40                  45

Asn Cys Ser Phe Arg Glu Ile Lys Thr Thr Leu Ala Lys Glu Asn Glu
 50                  55                  60

Val Leu Met Leu Lys Cys Pro Gln Leu Asp Asn Tyr Ile Leu Pro Trp
 65                  70                  75                  80

Lys Tyr Met Asn Arg Ser Glu Tyr Thr Val Thr Trp Lys Asn Ile Ser
                 85                  90                  95

Asn Ser Thr Glu Tyr Asn Asn Thr Arg Ile Glu Asn Asn Met Leu Met
            100                 105                 110

Phe Phe Pro Phe Tyr Asn Leu Gln Ala Gly Ser Lys Tyr Leu Cys Thr
        115                 120                 125

Val Ser Thr Asn Lys Ser Cys Asp Gln Ser Val Val Ile Val Lys Asn
130                 135                 140

Ser Phe Tyr Ser Asn Asn Cys Met Leu Ser Glu Ala Lys Glu Asn Asp
145                 150                 155                 160

Asn Phe Glu Ile Tyr Cys Gly Ile Leu His Ala Lys His Asn Thr Ile
                165                 170                 175

Lys Trp Phe Lys Glu Gly Lys Glu Ile Thr Asn Asn Tyr Lys Tyr Tyr
            180                 185                 190

Thr Lys Leu Gly Gly Tyr Val Lys Gly Ile Asn Asn Val Thr Tyr Ser
        195                 200                 205

Asp Ser Gly Lys Tyr Val Cys Lys Gly Tyr Tyr Ile Asp Val Leu Lys
210                 215                 220

Asn Ile Thr Tyr Thr Ala Lys Arg Cys Val Asn Leu Thr Val Ile Pro
225                 230                 235                 240

Asn Thr Tyr Tyr Asp Phe Phe Ile Val Asp Ile Pro Asn Val Thr Tyr
                245                 250                 255

Ala Lys Asn Asn Lys Lys Leu Glu Val Asn Cys Thr Ser Phe Val Asp
            260                 265                 270

Ile Asn Ser Tyr Asp Tyr Ile Leu Thr Ser Trp Leu Tyr Asn Gly Leu
        275                 280                 285

Tyr Leu Pro Leu Gly Val Arg Ile Tyr Gln Leu Tyr Ser Thr Asp Ile
290                 295                 300

Phe Phe Glu Asn Phe Ile Tyr Arg Thr Ser Thr Leu Val Phe Glu Asn
305                 310                 315                 320

Val Asp Ile Ser Asp Asp Asn Lys Thr Phe Glu Cys Glu Ala Leu Ser
                325                 330                 335

Val Thr Leu Lys Lys Ile Lys Tyr Thr Thr Ile Lys Val Glu Lys
            340                 345                 350

<210> SEQ ID NO 2
<211> LENGTH: 1056
<212> TYPE: DNA
<213> ORGANISM: yatapoxvirus
<220> FEATURE:
<221> NAME/KEY: misc_feature
<222> LOCATION: (1)..(1056)
<223> OTHER INFORMATION: Yaba-Like Disease Virus 136R gene (Y136 gene)

<400> SEQUENCE: 2
atgaaaatca catatataat acttctaata tgtaaagaaa taatatgtta caatagcggc      60
gatgatatgt atgattatat agcaaatgga aatattgatt atttaaaaac tattgataat     120
gatataataa atttagttaa taaaaactgc tcttttaggg aaataaaaac aacattagca     180

```
aaagaaaatg aagtgttaat gttaaaatgt cctcagttag ataattacat actaccctgg    240
aaatatatga acagatcgga atatactgtg acttggaaaa acattagcaa ctcaacagag    300
tataacaata ctagaataga aaataatatg ctaatgtttt ttccgtttta aatttgcaa     360 gcaggatcta agtatttatg tactgtttca actaacaaaa gctgtgatca agtgttgta     420 atagttaaaa actcttttta ttctaataat tgtatgttaa gtgaagcaaa ggaaaatgat    480
aattttgaaa tatattgtgg aatattacac gcaaaacata atactataaa atggtttaaa    540
gaaggaaaag aataactaa taactataaa tattacacaa agttaggtgg atatgtaaag     600
ggtataaaca acgttactta ttcagattct ggaaaatatg tctgcaaagg atattacatc    660
gacgtattaa aaatattac atatactgca aaaggtgtg taaatttgac agttattcct      720
aatacatatt acgatttttt tattgttgat attccaaacg ttacatatgc aaaaaataat    780
aaaaagttgg aagttaactg tacatctttt gtggatatta attcgtatga ttatatttta    840
actagttggt tatataacgg attgtactta cctttaggtg ttaggatata tcaattatac    900
agtaccgata tattttttga aaattttatt tatcgaacta gcacattggt atttgagaat    960
gtagatatat cagacgataa taaaacattt gaatgtgaag cgttatctgt aactctaaaa   1020
aaaataaaat atacaaccat taaagtagaa aaataa                             1056
```

<210> SEQ ID NO 3  
<211> LENGTH: 351  
<212> TYPE: PRT  
<213> ORGANISM: Vaccinia virus  
<220> FEATURE:  
<221> NAME/KEY: MISC_FEATURE  
<222> LOCATION: (1)..(351)  
<223> OTHER INFORMATION: Vaccinia Virus B18R protein

<400> SEQUENCE: 3

```
Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
            20                  25                  30

Phe Phe Asn Lys Met Arg Asp Thr Leu Pro Ala Lys Asp Ser Lys Trp
        35                  40                  45

Leu Asn Pro Ala Cys Met Phe Gly Gly Thr Met Asn Asp Ile Ala Ala
    50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
    130                 135                 140

Ser His Ile Arg Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His Tyr Asn Asn Ile Thr Trp Tyr Lys Asp Asn Lys Glu Ile
            180                 185                 190

Asn Ile Asp Asp Ile Lys Tyr Ser Gln Thr Gly Lys Glu Leu Ile Ile
```

-continued

```
                195                 200                 205
        His Asn Pro Glu Leu Glu Asp Ser Gly Arg Tyr Asp Cys Tyr Val His
            210                 215                 220

Tyr Asp Asp Val Arg Ile Lys Asn Asp Ile Val Val Ser Arg Cys Lys
        225                 230                 235                 240

Ile Leu Thr Val Ile Pro Ser Gln Asp His Arg Phe Lys Leu Ile Leu
                        245                 250                 255

Asp Pro Lys Ile Asn Val Thr Ile Gly Glu Pro Ala Asn Ile Thr Cys
                    260                 265                 270

Thr Ala Val Ser Thr Ser Leu Leu Ile Asp Asp Val Leu Ile Glu Trp
                275                 280                 285

Glu Asn Pro Ser Gly Trp Leu Ile Gly Phe Asp Phe Asp Val Tyr Ser
            290                 295                 300

Val Leu Thr Ser Arg Gly Gly Ile Thr Glu Ala Thr Leu Tyr Phe Glu
        305                 310                 315                 320

Asn Val Thr Glu Glu Tyr Ile Gly Asn Thr Tyr Lys Cys Arg Gly His
                        325                 330                 335

Asn Tyr Tyr Phe Glu Lys Thr Leu Thr Thr Val Val Leu Glu
                    340                 345                 350

<210> SEQ ID NO 4
<211> LENGTH: 1293
<212> TYPE: DNA
<213> ORGANISM: Vaccinia virus
<220> FEATURE:
<221> NAME/KEY: misc_feature
<222> LOCATION: (1)..(1293)
<223> OTHER INFORMATION: Vaccinia Virus B18R gene

<400> SEQUENCE: 4
gacaattaac gatctttata atatatcgta tccacctacc aaagtatagt tgtattttc      60 tcatgcgatg tgtgtaaaaa aactgatatt atataaatat tttagtgccg tataataaag    120
atgacgatga aaatgatggt acatatatat ttcgtatcat tattgttatt gctattccac    180
agttacgcca tagacatcga aaatgaaatc acagaattct tcaataaaat gagagatact    240
ctaccagcta aagactctaa atggttgaat ccagcatgta tgttcggagg cacaatgaat    300
gatatagccg ctctaggaga gccattcagc gcaaagtgtc ctcctattga agacagtctt    360
ttatcgcaca gatataaaga ctatgtggtt aaatgggaaa ggctagaaaa aaatagacgg    420
cgacaggttt ctaataaacg tgttaaacat ggtgatttat ggatagccaa ctatacatct    480
aaattcagta accgtaggta tttgtgcacc gtaactacaa agaatggtga ctgtgttcag    540
ggtatagtta gatctcatat tagaaaacct ccttcatgca ttccaaaaac atatgaacta    600
ggtactcatg ataagtatgg catagactta tactgtggaa ttctttacgc aaaacattat    660
aataatataa cttggtataa agataataag gaaattaata tcgacgacat taagtattca    720
caaacgggaa aggaattaat tattcataat ccagagttag aagatagcgg aagatacgac    780
tgttacgttc attacgacga cgttagaatc aagaatgata tcgtagtatc aagatgtaaa    840
atacttacgg ttataccgtc acaagaccac aggtttaaac taatactaga tccaaaaatc    900
aacgtaacga taggagaacc tgccaatata acatgcactg ctgtgtcaac gtcattattg    960
attgacgatg tactgattga atgggaaaat ccatccggat ggcttatagg attcgatttt   1020
gatgtatact ctgtttttaac tagtagaggc ggtattaccg aggcgacctt gtactttgaa   1080
aatgttactg aagaatatat aggtaataca tataaatgtc gtggacacaa ctattatttt   1140
```

```
gaaaaaaccc ttacaactac agtagtattg gagtaaatat acaatgcatt tttatataca   1200
ttactgaata attattatta ttatttatat cgtatttgtg ctataacgcg actatctagg   1260
tatttgtatc tcaccgatag agaacatata aat                                1293
```

<210> SEQ ID NO 5
<211> LENGTH: 556
<212> TYPE: PRT
<213> ORGANISM: Homo sapiens
<220> FEATURE:
<221> NAME/KEY: MISC_FEATURE
<222> LOCATION: (1)..(556)
<223> OTHER INFORMATION: Human IL1RL1 protein

<400> SEQUENCE: 5

```
Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ile Ala Val Cys
```

```
                325                 330                 335
Ser Val Phe Leu Met Leu Ile Asn Val Leu Val Ile Ile Leu Lys Met
            340                 345                 350

Phe Trp Ile Glu Ala Thr Leu Leu Trp Arg Asp Ile Ala Lys Pro Tyr
        355                 360                 365

Lys Thr Arg Asn Asp Gly Lys Leu Tyr Asp Ala Tyr Val Val Tyr Pro
    370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
            405                 410                 415

Leu Cys Ile Tyr Gly Arg Asp Met Leu Pro Gly Glu Asp Val Val Thr
        420                 425                 430

Ala Val Glu Thr Asn Ile Arg Lys Ser Arg His Ile Phe Ile Leu
    435                 440                 445

Thr Pro Gln Ile Thr His Asn Lys Glu Phe Ala Tyr Glu Gln Glu Val
450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
            485                 490                 495

Gln Asp Ser Leu Gln His Leu Met Lys Val Gln Gly Thr Ile Lys Trp
        500                 505                 510

Arg Glu Asp His Ile Ala Asn Lys Arg Ser Leu Asn Ser Lys Phe Trp
    515                 520                 525

Lys His Val Arg Tyr Gln Met Pro Val Pro Ser Lys Ile Pro Arg Lys
530                 535                 540

Ala Ser Ser Leu Thr Pro Leu Ala Ala Gln Lys Gln
545                 550                 555

<210> SEQ ID NO 6
<211> LENGTH: 2058
<212> TYPE: DNA
<213> ORGANISM: Homo sapiens
<220> FEATURE:
<221> NAME/KEY: misc_feature
<222> LOCATION: (1)..(2058)
<223> OTHER INFORMATION: Human IL1RL1 gene

<400> SEQUENCE: 6
aaagagaggc tggctgttgt atttagtaaa gctataaagc tgtaagagaa attggctttc      60
tgagttgtga aactgtgggc agaaagttga ggaagaaaga actcaagtac aacccaatga     120
ggttgagata taggctactc ttcccaactc agtcttgaag agtatcacca actgcctcat     180
gtgtggtgac cttcactgtc gtatgccagt gactcatctg gagtaatctc aacaacgagt     240
taccaatact tgctcttgat tgataaacag aatggggttt tggatcttag caattctcac     300
aattctcatg tattccacag cagcaaagtt tagtaaacaa tcatgggcc tggaaaatga     360 ggctttaatt gtaagatgtc ctagacaagg aaaacctagt tacaccgtgg attggtatta     420
ctcacaaaca aacaaagta ttcccactca ggaaagaaat cgtgtgtttg cctcaggcca     480
acttctgaag tttctaccag ctgcagttgc tgattctggt atttatacct gtattgtcag     540
aagtcccaca ttcaatagga ctggatatgc gaatgtcacc atatataaaa aacaatcaga     600
ttgcaatgtt ccagattatt tgatgtattc aacagtatct ggatcagaaa aaaattccaa     660
aatttattgt cctaccattg acctctacaa ctggacagca cctcttgagt ggtttaagaa     720
```

-continued

```
ttgtcaggct cttcaaggat caaggtacag ggcgcacaag tcattttggg tcattgataa    780
tgtgatgact gaggacgcag gtgattacac ctgtaaattt atacacaatg aaaatggagc    840
caattatagt gtgacggcga ccaggtcctt cacggtcaag gatgagcaag gcttttctct    900
gtttccagta atcggagccc ctgcacaaaa tgaaataaag gaagtggaaa ttggaaaaaa    960
cgcaaaccta acttgctctg cttgttttgg aaaaggcact cagttcttgg ctgccgtcct   1020
gtggcagctt aatggaacaa aaattacaga ctttggtgaa ccaagaattc aacaagagga   1080
agggcaaaat caaagtttca gcaatgggct ggcttgtcta gacatggttt taagaatagc   1140
tgacgtgaag gaagaggatt tattgctgca gtacgactgt ctggccctga atttgcatgg   1200
cttgagaagg cacaccgtaa gactaagtag gaaaaatcca attgatcatc atagcatcta   1260
ctgcataatt gcagtatgta gtgtattttt aatgctaatc aatgtcctgg ttatcatcct   1320
aaaaatgttc tggattgagg ccactctgct ctggagagac atagctaaac cttacaagac   1380
taggaatgat ggaaagctct atgatgctta tgttgtctac ccacggaact acaaatccag   1440
tacagatggg gccagtcgtg tagagcactt tgttcaccag attctgcctg atgttcttga   1500
aaataaatgt ggctatacct tatgcattta tgggagagat atgctacctg agaagatgt    1560
agtcactgca gtggaaacca acatacgaaa gagcaggcgg cacattttca tcctgacccc   1620
tcagatcact cacaataagg agtttgccta cgagcaggag gttgccctgc actgtgccct   1680
catccagaac gacgccaagg tgatacttat tgagatggag gctctgagcg agctggacat   1740
gctgcaggct gaggcgcttc aggactccct ccagcatctt atgaaagtac aggggaccat   1800
caagtggagg gaggaccaca ttgccaataa aaggtccctg aattctaaat tctggaagca   1860
cgtgaggtac caaatgcctg tgccaagcaa aattcccaga aaggcctcta gtttgactcc   1920
cttggctgcc cagaagcaat agtgcctgct gtgatgtgca aaggcatctg agtttgaagc   1980
tttcctgact tctcctagct ggcttatgcc cctgcactga agtgtgagga gcaggaatat   2040
taaagggatt caggcctc                                                 2058
```

<210> SEQ ID NO 7
<211> LENGTH: 31
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(31)
<223> OTHER INFORMATION: synthetic oligonucleotide for B18R

<400> SEQUENCE: 7

```
atggtaccga tgacgatgaa aatgatggta c                                    31
```

<210> SEQ ID NO 8
<211> LENGTH: 30
<212> TYPE: DNA
<213> ORGANISM: Artificial
<220> FEATURE:
<223> OTHER INFORMATION: Synthetic Oligonucleotide

<400> SEQUENCE: 8

```
cattctagat ttactccaat actactgtag                                      30
```

<210> SEQ ID NO 9
<211> LENGTH: 27
<212> TYPE: DNA

<213> ORGANISM: Artificial
<220> FEATURE:
<223> OTHER INFORMATION: Synthetic Oligonucleotide

<400> SEQUENCE: 9
gtagctagcc tccaatacta ctgtagt       27

<210> SEQ ID NO 10
<211> LENGTH: 29
<212> TYPE: DNA
<213> ORGANISM: Artificial
<220> FEATURE:
<223> OTHER INFORMATION: Synthetic oligonucleotide

<400> SEQUENCE: 10
ttggatcccc acagttacgc catagacat       29

<210> SEQ ID NO 11
<211> LENGTH: 30
<212> TYPE: DNA
<213> ORGANISM: Artificial
<220> FEATURE:
<223> OTHER INFORMATION: Synthetic Oligonucleotide

<400> SEQUENCE: 11
taggtaccat gaaaatcaca tatataatac       30

<210> SEQ ID NO 12
<211> LENGTH: 31
<212> TYPE: DNA
<213> ORGANISM: Artificial
<220> FEATURE:
<223> OTHER INFORMATION: Synthetic Oligonucleotide

<400> SEQUENCE: 12
ttgaattcat ttttctactt taatggttgt a       31

<210> SEQ ID NO 13
<211> LENGTH: 29
<212> TYPE: DNA
<213> ORGANISM: Artificial
<220> FEATURE:
<223> OTHER INFORMATION: Synthetic Oligonucleotide

<400> SEQUENCE: 13
tttgctagct ttttctactt taatggttg       29

<210> SEQ ID NO 14
<211> LENGTH: 28
<212> TYPE: DNA
<213> ORGANISM: Artificial
<220> FEATURE:
<223> OTHER INFORMATION: Synthetic Oligonucleotide

<400> SEQUENCE: 14
ctcggatccc aatagcggcg atgatatg       28

<210> SEQ ID NO 15
<211> LENGTH: 30
<212> TYPE: DNA
<213> ORGANISM: Artificial
<220> FEATURE:
<223> OTHER INFORMATION: Synthetic oligonucleotide

<400> SEQUENCE: 15
ttggtaccat gaccaacaag tgtctcctcc       30

<210> SEQ ID NO 16
<211> LENGTH: 30
<212> TYPE: DNA
<213> ORGANISM: Artificial
<220> FEATURE:
<223> OTHER INFORMATION: Synthetic Oligonucleotide

<400> SEQUENCE: 16
aggaattcag tttcggaggt aacctgtaag                               30

<210> SEQ ID NO 17
<211> LENGTH: 29
<212> TYPE: DNA
<213> ORGANISM: Artificial
<220> FEATURE:
<223> OTHER INFORMATION: Synthetic Oligonucleotide

<400> SEQUENCE: 17
tcaggtacca atggccctcc tgttccctc                                29

<210> SEQ ID NO 18
<211> LENGTH: 28
<212> TYPE: DNA
<213> ORGANISM: Artificial
<220> FEATURE:
<223> OTHER INFORMATION: Synthetic Oligonucleotide

<400> SEQUENCE: 18
atgaattcaa gatgagccca ggtctcta                                 28

<210> SEQ ID NO 19
<211> LENGTH: 34
<212> TYPE: DNA
<213> ORGANISM: Artificial
<220> FEATURE:
<223> OTHER INFORMATION: Synethetic Oligonucleotide

<400> SEQUENCE: 19
aaaggtacca tgattcaaaa gtgtttgtgg cttg                          34

<210> SEQ ID NO 20
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 20
ccgaattcat ttcctcctga atagagctgt aa                            32

<210> SEQ ID NO 21
<211> LENGTH: 31
<212> TYPE: DNA
<213> ORGANISM: Artificial
<220> FEATURE:
<223> OTHER INFORMATION: Synthetic Oligonucleotide

<400> SEQUENCE: 21
ccggtaccat gattatcaag cacttctttg g                             31

<210> SEQ ID NO 22
<211> LENGTH: 34
<212> TYPE: DNA
<213> ORGANISM: Artificial
<220> FEATURE:

<223> OTHER INFORMATION: Synthetic Oligonucleotide

<400> SEQUENCE: 22
ccgaattcct acctcgggct tctaaactct gtag					34

<210> SEQ ID NO 23
<211> LENGTH: 17
<212> TYPE: PRT
<213> ORGANISM: Artificial
<220> FEATURE:
<223> OTHER INFORMATION: Fusion protein tag amino acid sequence:
      His-Strep

<400> SEQUENCE: 23

His His His His His His Pro Asp His Trp Ser His Pro Gln Phe Glu
1               5                   10                  15

Lys

<210> SEQ ID NO 24
<211> LENGTH: 29
<212> TYPE: DNA
<213> ORGANISM: Artificial
<220> FEATURE:
<223> OTHER INFORMATION: Synthetic Oligonucleotide

<400> SEQUENCE: 24
atcgctagcc atttagaggt atttcctgg					29

<210> SEQ ID NO 25
<211> LENGTH: 29
<212> TYPE: DNA
<213> ORGANISM: Artificial
<220> FEATURE:
<223> OTHER INFORMATION: Synthetic Oligonucleotide

<400> SEQUENCE: 25
atcgctagcc atttggcaga ttctgctga					29

<210> SEQ ID NO 26
<211> LENGTH: 38
<212> TYPE: DNA
<213> ORGANISM: Artificial
<220> FEATURE:
<223> OTHER INFORMATION: Synthetic Oligonucleotide

<400> SEQUENCE: 26
attgggatcc taaacaatga aaatcacata tataatac					38

<210> SEQ ID NO 27
<211> LENGTH: 35
<212> TYPE: DNA
<213> ORGANISM: Artificial
<220> FEATURE:
<223> OTHER INFORMATION: Synthetic Oligonucleotide

<400> SEQUENCE: 27
taacaagctt cattattttt ctactttaat ggttg					35

<210> SEQ ID NO 28
<211> LENGTH: 569
<212> TYPE: PRT
<213> ORGANISM: Homo sapiens
<220> FEATURE:
<221> NAME/KEY: MISC_FEATURE
<222> LOCATION: (1)..(569)
<223> OTHER INFORMATION: Human IL1R1

<400> SEQUENCE: 28

```
Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Lys Ile Ile Leu
            20                  25                  30

Val Ser Ser Ala Asn Glu Ile Asp Val Arg Pro Cys Pro Leu Asn Pro
            35                  40                  45

Asn Glu His Lys Gly Thr Ile Thr Trp Tyr Lys Asp Asp Ser Lys Thr
        50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
                100                 105                 110

Phe Val Glu Asn Glu Pro Asn Leu Cys Tyr Asn Ala Gln Ala Ile Phe
            115                 120                 125

Lys Gln Lys Leu Pro Val Ala Gly Asp Gly Gly Leu Val Cys Pro Tyr
        130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
                180                 185                 190

Asn Tyr Thr Cys His Ala Ser Tyr Thr Tyr Leu Gly Lys Gln Tyr Pro
            195                 200                 205

Ile Thr Arg Val Ile Glu Phe Ile Thr Leu Glu Glu Asn Lys Pro Thr
        210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
        370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
```

-continued

```
                405                 410                 415
Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
            435                 440                 445

Arg Leu Ile Ile Ile Leu Val Arg Glu Thr Ser Gly Phe Ser Trp Leu
    450                 455                 460

Gly Gly Ser Ser Glu Glu Gln Ile Ala Met Tyr Asn Ala Leu Val Gln
465                 470                 475                 480

Asp Gly Ile Lys Val Val Leu Glu Leu Glu Lys Ile Gln Asp Tyr
                485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
        515                 520                 525

Arg Phe Trp Lys Asn Val Arg Tyr His Met Pro Val Gln Arg Arg Ser
    530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565
```

```
<210> SEQ ID NO 29
<211> LENGTH: 213
<212> TYPE: PRT
<213> ORGANISM: Variola virus
<220> FEATURE:
<221> NAME/KEY: MISC_FEATURE
<222> LOCATION: (1)..(213)
<223> OTHER INFORMATION: Variola Virus D9 Protein

<400> SEQUENCE: 29
```

```
Met Gly Ile Thr Met Asp Glu Glu Val Ile Phe Glu Thr Pro Arg Glu
1               5                   10                  15

Leu Ile Ser Ile Lys Arg Ile Lys Asp Ile Pro Arg Ser Lys Asp Thr
            20                  25                  30

His Val Phe Ala Ala Cys Ile Thr Ser Asp Gly Tyr Pro Leu Ile Gly
        35                  40                  45

Ala Arg Arg Thr Ser Phe Ala Phe Gln Ala Ile Leu Ser Gln Gln Asn
    50                  55                  60

Ser Asp Ser Ile Phe Arg Val Ser Thr Lys Leu Leu Arg Phe Met Tyr
65                  70                  75                  80

Tyr Asn Glu Leu Arg Glu Ile Phe Arg Arg Leu Arg Lys Gly Ser Ile
                85                  90                  95

Asn Asn Ile Asp Pro His Phe Glu Glu Leu Ile Leu Gly Gly Lys
            100                 105                 110

Leu Asp Lys Lys Glu Ser Ile Lys Asp Cys Leu Arg Arg Glu Leu Lys
        115                 120                 125

Glu Glu Ser Asp Glu Arg Ile Thr Val Lys Glu Phe Gly Asn Val Ile
    130                 135                 140

Leu Lys Leu Thr Thr Gln Asp Lys Leu Phe Asn Lys Val Tyr Ile Gly
145                 150                 155                 160

Tyr Cys Met Ser Cys Phe Ile Asn Gln Ser Leu Glu Asp Leu Ser His
                165                 170                 175

Thr Ser Ile Tyr Asn Val Glu Ile Arg Lys Ile Lys Ser Leu Asn Asp
            180                 185                 190
```

Cys Ile Asn Asp Asp Lys Tyr Glu Tyr Leu Ser Tyr Ile Tyr Asn Met
        195                 200                 205

Leu Val Asn Ser Lys
    210

<210> SEQ ID NO 30
<211> LENGTH: 189
<212> TYPE: PRT
<213> ORGANISM: Homo sapiens
<220> FEATURE:
<221> NAME/KEY: MISC_FEATURE
<222> LOCATION: (1)..(189)
<223> OTHER INFORMATION: Human IFN alpha

<400> SEQUENCE: 30

Met Ala Leu Ser Phe Ser Leu Leu Met Ala Val Leu Val Ser Tyr
1               5                   10                  15

Lys Ser Ile Cys Ser Leu Gly Cys Asp Leu Pro Gln Thr His Ser Leu
                20                  25                  30

Gly Asn Arg Arg Ala Leu Ile Leu Leu Ala Gln Met Gly Arg Ile Ser
                35                  40                  45

Pro Phe Ser Cys Leu Lys Asp Arg His Asp Phe Gly Leu Pro Gln Glu
    50                  55                  60

Glu Phe Asp Gly Asn Gln Phe Gln Lys Thr Gln Ala Ile Pro Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
                100                 105                 110

Tyr Gln Gln Leu Asn Asn Leu Glu Ala Cys Val Ile Gln Glu Val Gly
                115                 120                 125

Met Glu Glu Thr Pro Leu Met Asn Glu Asp Ser Ile Leu Ala Val Arg
                130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185

<210> SEQ ID NO 31
<211> LENGTH: 187
<212> TYPE: PRT
<213> ORGANISM: Homo sapiens
<220> FEATURE:
<221> NAME/KEY: MISC_FEATURE
<222> LOCATION: (1)..(187)
<223> OTHER INFORMATION: Human IFN beta

<400> SEQUENCE: 31

Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
                20                  25                  30

Ser Ser Asn Phe Gln Cys Gln Lys Leu Leu Trp Gln Leu Asn Gly Arg
                35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
                180                 185

<210> SEQ ID NO 32
<211> LENGTH: 166
<212> TYPE: PRT
<213> ORGANISM: Homo sapiens
<220> FEATURE:
<221> NAME/KEY: MISC_FEATURE
<222> LOCATION: (1)..(166)
<223> OTHER INFORMATION: Human IFN-gamma

<400> SEQUENCE: 32

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 33
<211> LENGTH: 208
<212> TYPE: PRT
<213> ORGANISM: Homo sapiens
<220> FEATURE:
<221> NAME/KEY: MISC_FEATURE
<222> LOCATION: (1)..(208)
<223> OTHER INFORMATION: Human IFN epsilon

<400> SEQUENCE: 33

Met Ile Ile Lys His Phe Phe Gly Thr Val Leu Val Leu Leu Ala Ser
1               5                   10                  15

Thr Thr Ile Phe Ser Leu Asp Leu Lys Leu Ile Ile Phe Gln Gln Arg
            20                  25                  30

Gln Val Asn Gln Glu Ser Leu Lys Leu Leu Asn Lys Leu Gln Thr Leu
        35                  40                  45

Ser Ile Gln Gln Cys Leu Pro His Arg Lys Asn Phe Leu Leu Pro Gln
    50                  55                  60

Lys Ser Leu Ser Pro Gln Gln Tyr Gln Lys Gly His Thr Leu Ala Ile
65                  70                  75                  80

Leu His Glu Met Leu Gln Gln Ile Phe Ser Leu Phe Arg Ala Asn Ile
                85                  90                  95

Ser Leu Asp Gly Trp Glu Glu Asn His Thr Glu Lys Phe Leu Ile Gln
            100                 105                 110

Leu His Gln Gln Leu Glu Tyr Leu Glu Ala Leu Met Gly Leu Glu Ala
        115                 120                 125

Glu Lys Leu Ser Gly Thr Leu Gly Ser Asp Asn Leu Arg Leu Gln Val
    130                 135                 140

Lys Met Tyr Phe Arg Arg Ile His Asp Tyr Leu Glu Asn Gln Asp Tyr
145                 150                 155                 160

Ser Thr Cys Ala Trp Ala Ile Val Gln Val Glu Ile Ser Arg Cys Leu
                165                 170                 175

Phe Phe Val Phe Ser Leu Thr Glu Lys Leu Ser Lys Gln Gly Arg Pro
            180                 185                 190

Leu Asn Asp Met Lys Gln Glu Leu Thr Thr Glu Phe Arg Ser Pro Arg
        195                 200                 205

<210> SEQ ID NO 34
<211> LENGTH: 207
<212> TYPE: PRT
<213> ORGANISM: Homo sapiens
<220> FEATURE:
<221> NAME/KEY: MISC_FEATURE
<222> LOCATION: (1)..(207)
<223> OTHER INFORMATION: Human IFN kappa

<400> SEQUENCE: 34

Met Ser Thr Lys Pro Asp Met Ile Gln Lys Cys Leu Trp Leu Glu Ile
1               5                   10                  15

Leu Met Gly Ile Phe Ile Ala Gly Thr Leu Ser Leu Asp Cys Asn Leu
            20                  25                  30

Leu Asn Val His Leu Arg Arg Val Thr Trp Gln Asn Leu Arg His Leu
        35                  40                  45

Ser Ser Met Ser Asn Ser Phe Pro Val Glu Cys Leu Arg Glu Asn Ile
    50                  55                  60

Ala Phe Glu Leu Pro Gln Glu Phe Leu Gln Tyr Thr Gln Pro Met Lys
65                  70                  75                  80

Arg Asp Ile Lys Lys Ala Phe Tyr Glu Met Ser Leu Gln Ala Phe Asn
                85                  90                  95

Ile Phe Ser Gln His Thr Phe Lys Tyr Trp Lys Glu Arg His Leu Lys
            100                 105                 110

```
Gln Ile Gln Ile Gly Leu Asp Gln Gln Ala Glu Tyr Leu Asn Gln Cys
        115                 120                 125

Leu Glu Glu Asp Lys Asn Glu Asn Glu Asp Met Lys Glu Met Lys Glu
        130                 135                 140

Asn Glu Met Lys Pro Ser Glu Ala Arg Val Pro Gln Leu Ser Ser Leu
145                 150                 155                 160

Glu Leu Arg Arg Tyr Phe His Arg Ile Asp Asn Phe Leu Lys Glu Lys
                165                 170                 175

Lys Tyr Ser Asp Cys Ala Trp Glu Ile Val Arg Val Glu Ile Arg Arg
                180                 185                 190

Cys Leu Tyr Tyr Phe Tyr Lys Phe Thr Ala Leu Phe Arg Arg Lys
        195                 200                 205

<210> SEQ ID NO 35
<211> LENGTH: 195
<212> TYPE: PRT
<213> ORGANISM: Homo sapiens
<220> FEATURE:
<221> NAME/KEY: MISC_FEATURE
<222> LOCATION: (1)..(195)
<223> OTHER INFORMATION: Human IFN omega

<400> SEQUENCE: 35

Met Ala Leu Leu Phe Pro Leu Leu Ala Ala Leu Val Met Thr Ser Tyr
1               5                   10                  15

Ser Pro Val Gly Ser Leu Gly Cys Asp Leu Pro Gln Asn His Gly Leu
            20                  25                  30

Leu Ser Arg Asn Thr Leu Val Leu Leu His Gln Met Arg Arg Ile Ser
        35                  40                  45

Pro Phe Leu Cys Leu Lys Asp Arg Arg Asp Phe Arg Phe Pro Gln Glu
    50                  55                  60

Met Val Lys Gly Ser Gln Leu Gln Lys Ala His Val Met Ser Val Leu
65                  70                  75                  80

His Glu Met Leu Gln Gln Ile Phe Ser Leu Phe His Thr Glu Arg Ser
                85                  90                  95

Ser Ala Ala Trp Asn Met Thr Leu Leu Asp Gln Leu His Thr Gly Leu
            100                 105                 110

His Gln Gln Leu Gln His Leu Glu Thr Cys Leu Leu Gln Val Val Gly
        115                 120                 125

Glu Gly Glu Ser Ala Gly Ala Ile Ser Ser Pro Ala Leu Thr Leu Arg
    130                 135                 140

Arg Tyr Phe Gln Gly Ile Arg Val Tyr Leu Lys Glu Lys Lys Tyr Ser
145                 150                 155                 160

Asp Cys Ala Trp Glu Val Val Arg Met Glu Ile Met Lys Ser Leu Phe
                165                 170                 175

Leu Ser Thr Asn Met Gln Glu Arg Leu Arg Ser Lys Asp Arg Asp Leu
                180                 185                 190

Gly Ser Ser
        195
```

INTERFERON ANTAGONISTS, ANTIBODIES THERETO AND ASSOCIATED METHODS OF USE

CROSS-REFERENCE TO RELATED APPLICATIONS

Figure 1:
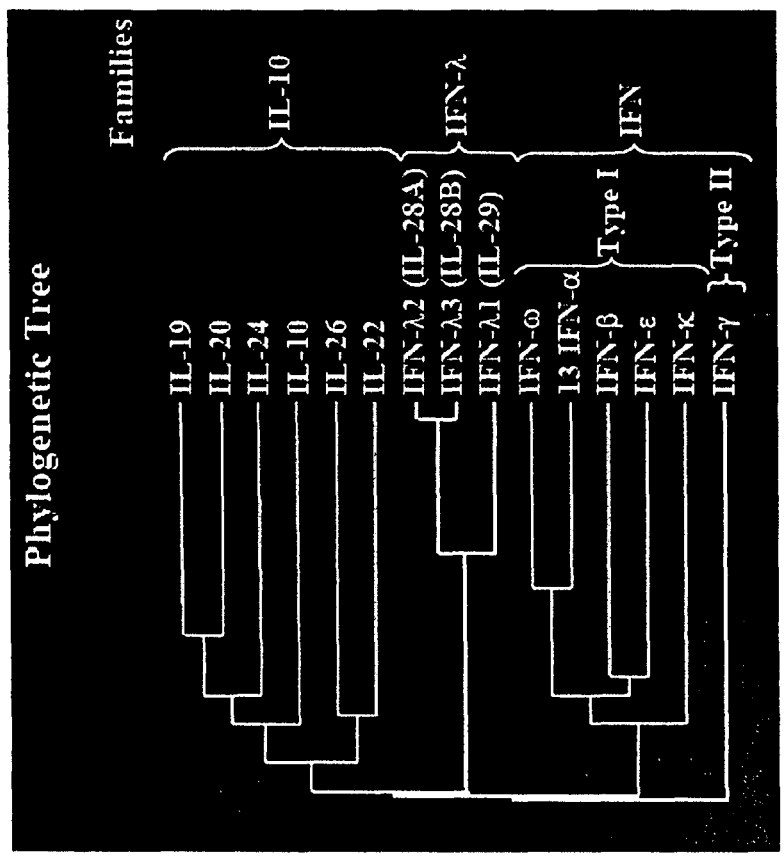

Under 35 U.S.C. §119(e) this application claims the benefit of U.S. Provisional Application No. 60/839,499 filed Aug. 23, 2006, which is hereby incorporated by reference in its entirety.

STATEMENT REGARDING FEDERALLY SPONSORED RESEARCH

The U.S. Government has certain rights in this invention pursuant to Grant No.: RO1 AI51139 (Apr. 1, 2001-Mar. 31, 2006), and Grant No.: RO1 AI057468 (Dec. 16, 2004-Oct. 30, 2009); to Sergei Kotenko, awarded by the National Institutes of Health (NIH), National Institute of Allergy and Infectious Diseases (NIAID).

INCORPORATION BY REFERENCE

In compliance with 37 C.F.R. §1.52(e)(5), the sequence information contained on compact disc, file name: Kotenko_2007utility_ST25.txt; size 39 KB; created on: 22 Aug., 2007; using PatentIn-3.4, and Checker 4.4.0 is hereby incorporated by reference in its entirety. The Sequence Listing information recorded in computer readable form (CRF) is identical to the written Sequence Listing provided herewith. The data in the paper copy of the Sequence Listing, and Computer Readable Form of the Sequence Listing submitted herewith contain no new matter, and are fully supported by the priority application, U.S. Provisional Patent Application No. 60/839,499.

FIELD OF THE INVENTION

The present invention relates to compositions comprising one or more interferon antagonists and methods of utilizing said compositions to modulate the interferon immune response.

BACKGROUND

Interferons (IFNs) are proteins produced by the cells of the immune system of most vertebrates in response to challenges by foreign agents such as viruses, bacteria, parasites, tumor cells, and donor tissue. Interferons belong to the large class of glycoproteins known as cytokines. Three types of IFNs (Type I, II, and III) have been described which signal through unique receptor heterodimers. Because IFNs are robustly produced in response to viruses and have widespread effects on most cells of the immune system, IFNs are considered important molecules in linking early or innate immune responses to infection with later adaptive immune responses.

Since the discovery of IFN in 1957 as a substance able to induce resistance to viral infection, IFNs are now known as pleiotropic cytokines with diverse activities, ranging from the induction of viral resistance in cells, to the regulation of both innate and adaptive arms of the immune response. Antiviral activities of IFNs are often accompanied by anti-proliferative and pro-apoptotic effects in various cells. IFNs also upregulate MHC(HLA) class I antigen expression and induce expression of immunoproteasome subunits. These IFN activities modulate antigen presentation in virus-infected cells, making these cells a better target for CD8+ cytotoxic T cells (CTLs).

IFNs are also major activators of natural killer (NK) cells and CTLs, both of which act on virus-infected cells, or cells with other intracellular pathogens. IFNs promote the differentiation of monocytes into monocytic or common dendritic cells, the major antigen-presenting cell. IFNs have direct effects on B-cell maturation and class-switching, and are also recognized for their antitumor activities. Presently, IFNs are used clinically as a treatment for several malignancies, including cancer.

However, the potency and pleiotropic effects of IFNs requires that they be maintained under tight transcriptional regulation, with the normal state of most genes being "off". Transcription up-regulation for most classical type I IFNs is subject to sophisticated systems that monitor the presence of viruses or other pathogen-related stimuli and provide robust and well-tuned production of type I IFNs. Expression of type III IFNs appears to be regulated through the similar pathways. Recent data suggest involvement of IFNs in the pathogenesis of some immune diseases, for example, autoimmune diseases, systemic lupus erythematosus (SLE), and Sjögren's syndrome; acute allograft rejections; septic shock; and exaggerated antiviral response induced by certain viruses or viral strains.

Viruses have developed many strategies to circumvent IFN-induced antiviral protection, generally interfering with IFN signaling. Poxviruses form a large family of double-strand DNA viruses. Some poxviruses are extremely virulent, and include variola virus (VARV) which causes smallpox with high mortality rate, as well as the genetically related vaccinia virus (VACV). VACV encodes two secreted proteins which function as IFN antagonists: B8R protein is the soluble receptor of IFN-γ, whereas B18R protein binds IFN-α, IFN-β and IFN-ω and suppresses interaction of IFNs with their membrane-bound receptor complexes. Most poxviruses encode proteins homologous to vacvB18R which are predicted to possess similar abilities to neutralize IFN-α/β.

The Yaba-like disease virus (YLDV), which causes vesicular skin lesions in primates and can be transmitted to humans, encodes the 136R protein which bears slight homology (about 27%) to vacvB18R protein. However, the ability of yldv136R to inhibit biological activities of IFNs, or the ability of vacvB18R to neutralize type III IFNs and novel members of the type I IFN family, IFN-κ and IFN-γ is currently unknown.

Due to the involvement of interferons in many immunological conditions, the IFN signaling pathway remains highly relevant as a target for further research as well as therapeutic intervention. Not surprisingly, the discovery of an INF antagonist agent that exhibits specificity for IFN proteins, especially those of multiple types, would be valuable as a therapeutic for treating disorders caused by hyper-stimulation of the IFN signaling system. For example, there are currently no known antagonists of type III interferons. On the other hand, agents that are antagonists of viral INF receptors are potentially useful for the treatment and prevention of viral infection and proliferation.

SUMMARY

The present invention is based on the surprising and unexpected discovery that the Yaba-like Disease Virus (YLDV) encodes a protein, Y136, which serves as a receptor for interferon proteins, in particular, type I and III interferons. As an IFN antagonist, isolated Y136 polypeptides, nucleic acids, and antibodies are valuable as therapeutics for IFN-related disorders, and as research tools for further discovery relating to IFN physiology.

Therefore, certain aspects of the present invention relate to compositions comprising isolated Y136 polypeptides, and the nucleic acid constructs encoding them, and associated methods of use, for example, as antagonists of IFN activity. This aspect also encompasses recombinant cloning and expression vectors containing Y136 nucleic acids operably linked to one or more transcription regulatory elements. In an additional aspect, the invention relates to host cells into which the Y136 nucleic acid constructs has been introduced.

In a related aspect, the invention relates to Y136 receptor compositions, for example, an antibody or fragment thereof, which is specific for a Y136 epitope, and associated methods of use. The Y136 receptor of the invention is useful as a prophylactic or treatment for viral infections.

Additional objects and advantages of the present invention will be appreciated by one of ordinary skill in the art in light of the instant drawings, detailed description, examples, and claims. These additional objects and advantages are expressly included within the scope of the present invention.

BRIEF DESCRIPTION OF THE DRAWINGS

FIG. 1 Type I and type III IFNs, their viral and cellular receptors and their homologs. Phylogenetic trees were generated by alignment of aa sequences of the following proteins: (A) VACV-encoded soluble type I IFN antagonist (B18), B18 orthologues encoded by VARV (D9) and by YLDV (Y136), and the extracellular domains of the ligand binding chains of the type I and type III IFN receptor complexes (IFN-αR2 and IFN-λR1, respectively), and several members of the IL-1 receptor family (IL-1 receptor 1 (IL-1R1), IL-1 receptor 2 (IL-1R2), IL-1 receptor like 1 (IL-1RL1), IL-1 receptor accessory protein (IL-1RAP), IL-1 receptor accessory protein like 1 (IL-1RAPL1), and IL-18 receptor 1 (IL-18R1); and (B) type I (IFN-α, IFN-β, IFN-ω, IFN-κ and IFN-ϵ; only one IFN-α was used in alignment because the thirteen human IFN-α species are highly conserved) and type III (IFN-λ1, IFN-λ2 and IFN-λ3) IFNs. Because of the low sequence identity, the trees are subject to small changes in the alignment, and are therefore instructive, not definitive. (C) Alignments of aa sequences of viral proteins (B18 and Y136) and human IL1R1s, and the extracellular domain of IL1R1 are presented. Consensus sequence is shown on the bottom. Identical and similar aa corresponding to the consensus sequence are underlined. (D) Phylogenetic tree of CRF2 cytokine family of paralogous cytokine proteins.

FIG. 2 Y136 is a secreted glycoprotein that inhibits primate type I IFNs. (A) BS-C-1 cells were infected with the indicated VACVs and the proteins in the conditioned supernatants were analyzed by immunoblotting with hemagglutinin (HA) mAb. The molecular mass markers are shown on the right. (B-F) Different amounts of conditioned supernatants from cells infected with the indicated viruses were mixed with human IFN-α (B), human IFN-β (C), mouse IFN-α (D), mouse IFN-β (E) or rhesus monkey IFN-α (F) and the ability of the mixture to inhibit plaque formation by Cocal virus was determined as described in Methods. Data are expressed as the percentage inhibition of IFN antiviral activity from duplicate experiments.

FIG. 3 Expression of B18 and Y136 proteins from mammalian cells. Conditioned medium (1 ml) from COS cells (lanes 1, 3, 5 and 7, mock), and COS cells transfected with plasmids pEF-B18R-FL (lanes 2 and 4, B18-FL), and pEF-SPFL-Y136 (lanes 6 and 8, FL-Y136) were immunoprecipitated with FLAG antibody and analyzed by immunoblotting with FLAG mAb. Before immunoblotting, samples 3, 4, 7 and 8 were treated with PNGase F to remove N-linked carbohydrates. The molecular mass markers are shown on the left.

FIG. 4 IFN-κ and IFN-ϵ signal through canonical type I IFN receptor complex. (A) Two hamster cell lines (αR/γR cells, right panel; and λR/γR cells, left panel) expressing modified human type I and type III IFN receptor complexes are shown schematically. The αR/γR cells express chimeric IFN-αR2/IFN-γR1 (αR2/γR1) and IFN-αR1/IFN-γR2 (αR1/γR2) receptor chains; and λR/γR cells express chimeric IFN-αR1/IFN-γR1 (λR1/γR1) and intact IL-10R2 chains. (B) The response of the parental, αR/γR1 and λR/γR hamster cells to various type I and type III IFNs was evaluated by measuring IFN-induced STAT1 activation in EMSA. The cells were left untreated or treated with various stimuli: recombinant *E. coli*-produced human IFN-α2 (α; 1,000 units/ml 4 ng/ml) and IFN-λ1 (λ; 4 ng/ml), or conditioned medium from COS cells transfected with plasmids encoding either human IFN-β (β), IFN-ω (ω), IFN-κ (κ), IFN-ϵ (ϵ) or hamster IFN-γ (γ; 100 μl). Each type I IFN was used at a concentration of 1,000 IFN-α-equivalent units/ml, as determined by their antiviral potency on human cells and the ability to induce STAT activation in comparison with standard IFN-α2.

FIG. 5 Effects of B18 protein on IFN signaling and biological activities. (A) αR/γR and λR/γR cells were left untreated or treated with 1,000 units/ml of various type I IFNs (recombinant IFN-α2 (α) and COS cell produced IFN-β (β), IFN-ω (ω), IFN-ω (ω) and IFN-ϵ (ϵ)) or recombinant IFN-λ1 (λ; 4 ng/ml) with or without COS cell conditioned medium containing B18-FL protein (100 μl). STAT1 activation in cells was then evaluated by EMSA. (B) Antiviral protection in response to type I and type III IFNs with or without B18 was evaluated on HT-29 cells infected with VSV with a cytopathic effect (CPE) reduction assay. The ordinate represents the fold increase of the amount of IFNs required to achieve 50% protection against virus-induced CPE in the presence of B18 (50 μl of COS cell conditioned medium containing B18 in a total volume of 250 μl/well) versus in its absence. (C) The inhibition by B18 of IFN-induced MHC class I antigen expression in HT-29 cells was evaluated by flow cytometry. The level of IFN-induced MHC class I antigen expression in the presence of B18 (100 μl of COS cell conditioned medium containing B18 in 2 ml assay volume) is shown as a percentage of the IFN-induced (without B18; type I IFNs—1,000 un/ml, IFN-λ1—4 ng/ml) over the basal level of MHC class I antigen expression.

FIG. 6 Effect of Y136 protein on IFN signaling and biological activities. (A) αR/γR and λR/γR cells were left untreated or treated with 1,000 units/ml of various type I IFNs (recombinant IFN-α2 (α) and COS cell-produced IFN-β (β), IFN-ω (ω), IFN-κ (κ) and IFN-κ (κ)) or recombinant IFN-λ1 (λ; 4 ng/ml) with or without COS cell conditioned medium containing FL-Y136 (100 μl). STAT1 activation in cells was evaluated by EMSA. (B) Antiviral protection in response to type I and type III IFNs with (50 μl of COS cell conditioned medium containing Y136 in a total volume of 250 μl/well) or without Y136 protein was evaluated on HT-29 cells infected with VSV with a cytopathic effect (CPE) reduction assay. The ordinate represents the fold increase of the amount of IFNs required to achieve 50% protection against virus-induced CPE in the presence versus in the absence of Y136. (C) the inhibitory effect of Y136 on the level of IFN-induced MHC class I antigen expression in HT-29 cells was evaluated by flow cytometry. The level of IFN-induced MHC class I antigen expression in the presence of Y136 protein (100 μl of COS cell conditioned medium containing Y136 protein in 2 ml assay volume) is shown as a percentage of the IFN-induced (without Y136; type I IFNs—1,000 un/ml, IFN-λ1—4 ng/ml) over the basal level of MHC class I antigen expression. (D) HT-29, 10R/γR and 22R/γR cells were left untreated or treated with 4 ng/ml of recombinant IFN-γ, IL-10 and IL-22, respectively, with or without COS cell conditioned medium containing either B18-FL or FL-Y136 protein (1000), and STAT1 activation in cells was evaluated by EMSA.

Figure 7:
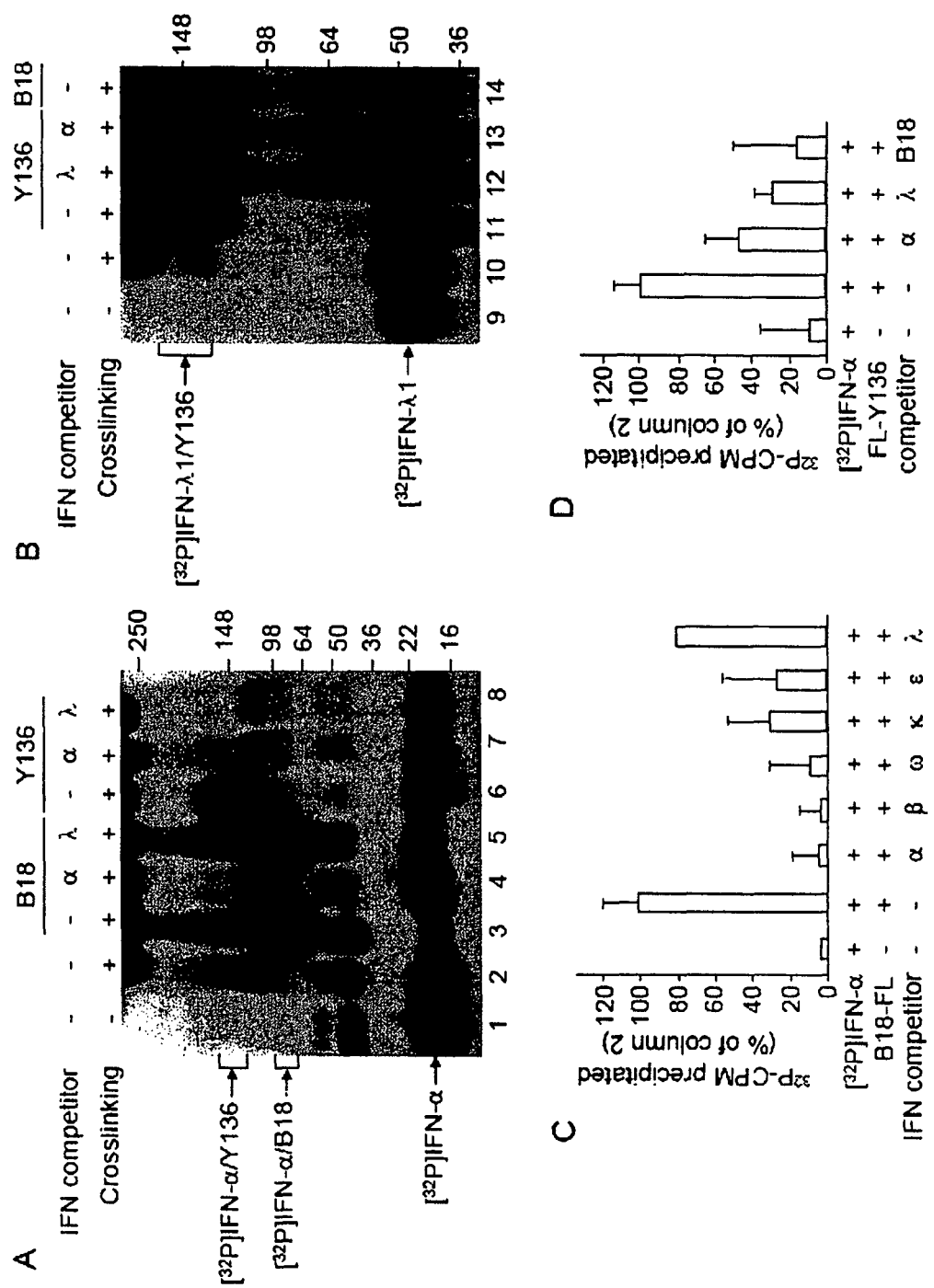

FIG. 7 Crosslinking of IFNs to viral receptors and competition experiments. (A and B) Untreated [$^{32}$P]-IFN-α2-P and [$^{32}$]-His-Strep-IFN-λ1-P were loaded as controls (lanes 1 and 9). [$^{32}$P]-labeled IFNs were crosslinked in solution in the absence of viral receptors (lanes 2 and 10) and to either B18-FL or FL-Y136 proteins with (lanes 4, 5, 7, 8, 12, and 13) or without (lanes 3, 5, 11 and 14) addition of a 100-fold excess of unlabeled competitor IFN-α2 or IFN-λ1, as indicated (FL=FLAG tag octapeptide). The crosslinked complexes were analyzed by SDS-PAGE. Positions of molecular mass markers are shown on the right. (C and D) Immunoprecipitation of complexes of [$^{32}$P]-IFN-α2-P and either B18-FL of FL-Y136 was performed with FLAG antibody. Non-radioactive IFNs or B18 without a FLAG tag were used as competitors. The amount of [$^{32}$P]-IFN-α2 precipitated in the presence of competitors is shown as a percentage of the amount of [$^{32}$P]-IFN-α2 precipitated with either B18-FL or FL-Y136; the background amount of [$^{32}$P]-IFN-α2 precipitated without viral receptors was subtracted.

Figure 8:
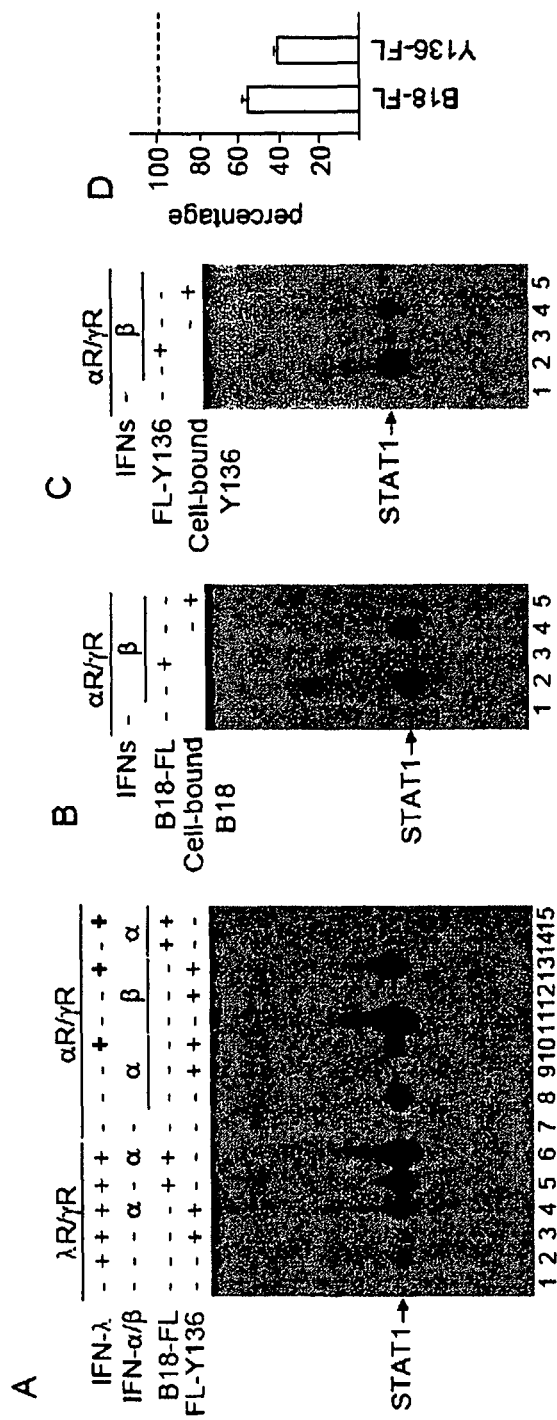

FIG. 8 Interaction of viral IFN antagonists with IFNs. (A) λR/γR and αR/γR cells were left untreated (lanes 1 and 7) or treated with IFN-λ1 (4 ng/ml; lanes 2-6) or IFN-α2 (α; lanes 8-10, 14 and 15) and IFN-β (β; lanes 11-13), respectively, with (+) or without (−) COS cell produced FL-Y136 or B18-FL protein (100 μl). Where indicated (bold letters) the excess of IFN-α2 (10,000 un/ml; α; lanes 4 and 6) was added to λR/γR cells, or the excess of IFN-λ1 (100 ng/ml; +; lanes 10, 13 and 15) was added to αR/γR cells. IFN-induced STAT1 activation in cells was evaluated by EMSA. (B and C) COS cells were transfected with expression plasmids for either B18 (cell-bound B18; +; lane 5 in B) or Y136 (cell-bound Y136; +; lane 5 in C), or were mock transfected (cell bound receptors; −; lanes 4 in B and C) and were incubated with IFN-β (1,000 un/ml; β; lanes 4 and 5) in 100 μl of medium for 1 h. COS cells were removed by centrifugation and cell-free supernatant was used to treat αR/γR cells. In control assays, αR/γR cells were left untreated (lanes 1) or treated with IFN-β (1,000 un/ml; β; lanes 2 and 3) with (lanes 3) or without (lanes 2) soluble COS cell produced B18-FL or FL-Y136 and STAT1 activation in cells was evaluated by EMSA. (D) The inhibitory effect of B18 or Y136 on the basal level of MHC class I antigen expression was evaluated by flow cytometry. The basal level of MHC class I antigen expression in HT-29 cells expressing viral proteins is shown as a percentage of the basal level of MHC class I antigen expression in parental HT-29 cells.

Figure 9:
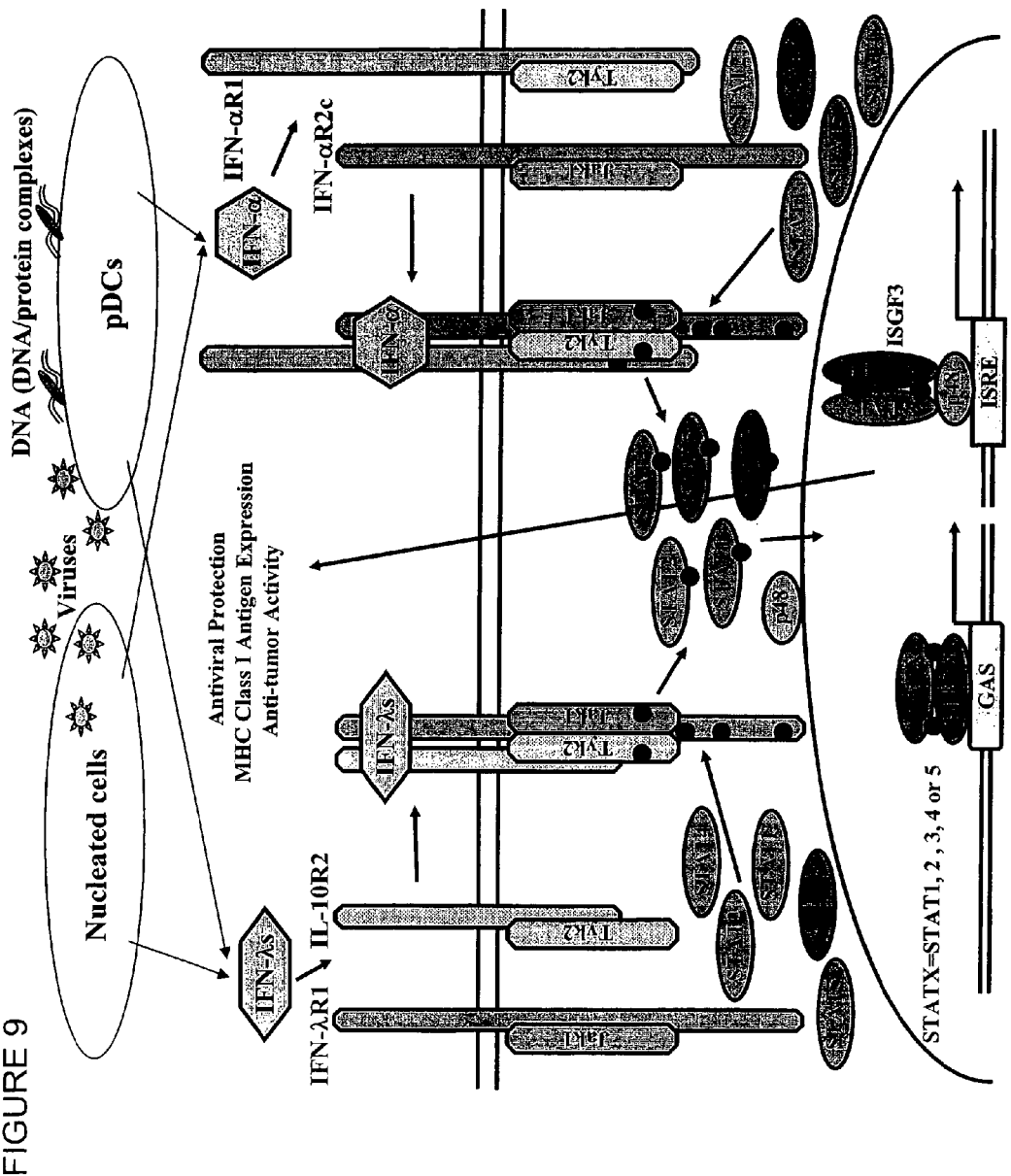

FIG. 9 Models of type III INF (IFN-λ) and type I IFN (IFN-α/β) receptor systems. IFN-λs and type I IFNs use distinct heterodimeric receptor complexes. The IFN-λs engage the unique IFN-λR1 and IL-10R2, a subunit also used by the IL-10 and IL-22 receptor complexes. In contrast, IFN-αR1 and IFN-αR2c form the active type I IFN receptor complex. Ligand binding leads to the formation of the heterodimeric receptor complex and to the initiation of a signal transduction cascade involving member of the Jak protein kinase family and the STAT family of transcription activators. IL-10R2 and IFN-αR1 chains are associated with Tyk2, whereas IFN-αR1c and IFN-λR1 interact with Jak1. Upon ligand-mediated heterodimerization of INF-λ or IFN-α receptor chains, receptor-associated Jaks cross-activate each other, phosphorylate the IFN-λR1 or IFN-αR2c intracellular domains and, thus initiate the cascade of signal transduction events. Similar sets of STAT proteins, STAT1, STAT2, STAT3, STAT4, and STAT5 are activated by IFN-λ and IFN-α leading to activation of overlapping biological activities, such as upregulation of MHC class I antigen expression, induction of antiviral protection and anti-tumor activity.

FIG. 10 Type I and type III IFNs, their viral and cellular receptors and their orthologues. Phylogenetic trees were generated by alignment of aa sequences of the following proteins: (A) viral IFN antagonists B18, Y136, and a B18 ortholog encoded by VARV (D9), and the extracellular domains of the ligand binding chains of the type I and type III IFN receptor complexes (IFN-αR2 and IFN-λR1), and several members of the IL-1 receptor family (members of the immunoglobulin superfamily): IL-1 receptor 1 (IL1R1), IL-1 receptor 2 (IL1R2), IL-1 receptor like 1 (IL1RL1), IL-1 receptor accessory protein (IL1RAP), IL-1 receptor accessory protein like 1 (IL1RAPL1), and IL-18 receptor 1 (IL-18R1); and (B) type I (IFN-α, IFN-β, IFN-ω, IFN-κ and IFN-ε; only one IFN-α was used in alignment because the thirteen human IFN-α species are highly conserved) and type III (IFN-λ1, IFN-λ2 and IFN-λ3) IFNs. Consensus sequence is shown on the bottom. Identical as corresponding to the consensus sequence are shown in black outline with white lettering. Similar aa are shown in gray outline with white lettering.

Figure 11:
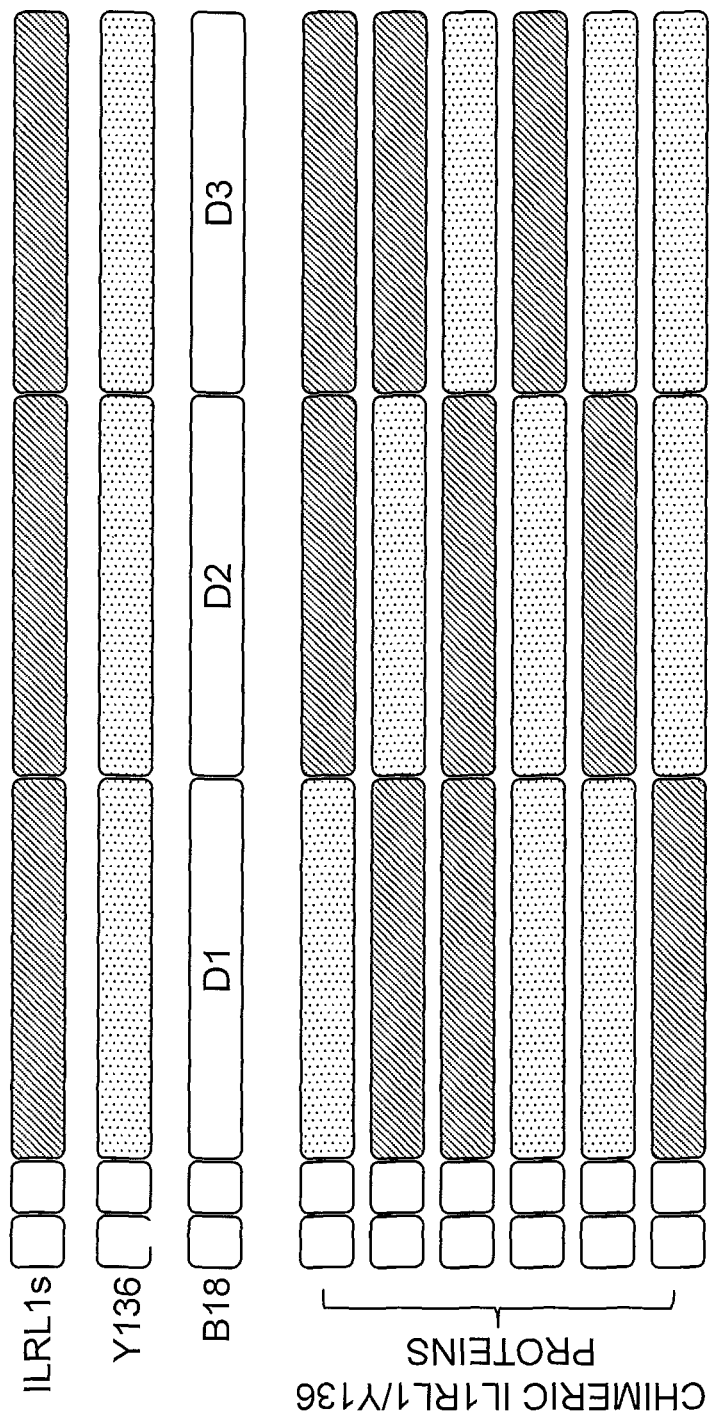

FIG. 11 Design of chimeric proteins. Structures of FL-IL1RL1s, FL-Y136, FL-B18, and chimeric IL1RL1/Y136 proteins are schematically shown. Each protein is composed of three immunoglobulin-like (Ig-1) domains (D1, D2, and D3). SP represents a signal peptide that will be removed in secreted proteins leaving the FLAG epitope (FL) at the amino terminus of mature proteins.

DETAILED DESCRIPTION

Type I (IFN-α/β) and type III (IFN-λs) interferons (IFNs) are important components of the host antiviral response. Type III IFNs are effective against several viruses in epithelial-like cells expressing type III IFN receptors. Moreover, expression of type III IFNs by VACV causes dramatic virus attenuation in mice, showing that type III IFNs can be important in vivo and might be used for the treatment of poxvirus infections. Nevertheless, the functional significance of type III IFNs against many viruses and their relative importance compared to type I IFNs remains largely uncharacterized, and no specific antagonist mechanism targeting type III IFNs has yet been described.

The present description details the surprising and unexpected discovery that the Yaba-like Disease Virus (YLDV) encodes a protein, Y136, which serves as a specific receptor for both type I and type III interferons. As presently described, besides demonstrating the capacity to bind type I interferons, Y136 is one of the only known antagonists of type III interferons. As such, the instant invention describes proteins, nucleic acids, antibodies, and chemical agents useful as therapeutics, diagnostics, or research tools for aiding in the understanding of interferon physiology.

The nucleic acid molecules of the instant invention, individually, or in combination or in conjunction with other drugs, can be used to treat diseases or conditions discussed below. For example, the subject can be treated, or other appropriate cells can be treated, as is evident to those skilled in the art, individually or in combination with one or more drugs under conditions suitable for the treatment.

The present invention provides novel nucleotides and polypeptides encoded thereby. The sequences are collectively referred to herein as "Y136 nucleic acids" or "Y136 polynucleotides" and the corresponding encoded polypeptides are referred to as "Y136 polypeptides" or "Y136 proteins." Unless indicated otherwise, "Y136" or "136R" is meant to refer to any of the novel sequences disclosed herein.

As used herein, the term "IFN antagonist" or "antagonist of IFN" is used generally to refer to an agent capable of direct or indirect inhibition of IFN expression, binding, and/or activity. Also, as used herein "IFN receptor" relates generally to any protein or fragment thereof capable of undergoing binding to an IFN protein.

By "modulate" is meant that the expression of the gene, or level of RNAs or equivalent RNAs encoding one or more proteins, or activity of one or more proteins is up-regulated or down-regulated, such that the expression, level, or activity is greater than or less than that observed in the absence of the nucleic acid molecules of the invention.

By "gene" it is meant a nucleic acid that encodes RNA, for example, nucleic acid sequences including but not limited to a segment encoding a polypeptide.

Y136 (or "136R") from Yaba-like disease virus, a yatapoxvirus, is a secreted glycoprotein related to protein B18 from Vaccinia virus, a known type I IFN binding protein and a member of the immunoglobulin superfamily. (Gene Symbol/GenBank Accession Number for Y136 protein: AJ293568). Surprisingly, whereas B18 inhibits only type I IFNs, Y136 inhibits both type I and type III IFNs. Y136 inhibits IFN-induced signaling and suppresses IFN-mediated biological activities including up-regulation of MHC class I antigen expression and induction of the antiviral state. These data demonstrate that poxviruses have developed unique strategies to counteract IFN-mediated antiviral protection and highlight the importance of type III IFNs in antiviral defense. These results suggest that type III IFNs may be an effective treatment for some poxyiral infections.

Interferons (IFNs) are defined by their ability to induce resistance to viral infection. Three types of IFNs have been described that signal through unique receptor heterodimers. However, all IFN receptor subunits demonstrate limited amino acid (aa) similarity in their extracellular domains and belong to the class II cytokine receptor family (CRF2).

Human type I IFNs include the well characterized 13 IFN-α proteins, IFN-β, IFN-ω and the more recently identified IFN-κ and IFN-ϵ. Type I IFNs signal through a common cellular IFN-α/β receptor complex, although the receptor subunits used and the precise signaling of IFN-κ and IFN-ϵ are less well characterized. The IFN-α/β receptor complex is composed of two unique subunits, IFN-αR1 and IFN-αR2. Both receptor subunits are required to assemble the functional receptor complex for IFN-α, IFN-β and IFN-ω. Antibody-mediated neutralization of IFN-αR2 blocked IFN-α signaling, demonstrating the requirement for IFN-αR2. However, participation of IFN-αR1 subunit in the IFN-κ receptor complex has not been demonstrated. The signaling and the receptor components for IFN-ϵ are unknown.

IFN-γ is the sole type II IFN. It binds to an IFN-γ receptor complex and induces cellular (Th1) immune response, such as the production of cytotoxic T lymphocytes that are important for destruction of virus-infected cells. The IFN-γ receptor complex consists of unique IFN-γR1 and IFN-γR2 chains.

Type III IFNs were discovered recently and are IFN-λ1, IFN-λ2 and IFN-λ3 (Kotenko et al, 2003), also known as interleukin (IL)-29 and IL-28A and IL-28B, respectively (Sheppard et al, 2003). They signal through an IFN-λ receptor complex composed of a unique IFN-λR1 chain and a shared IL-10R2 chain that is also the second subunit of the IL-10, IL-22 and IL-26 receptor complexes (Kotenko et al, 2004). The downstream signaling events induced by type III IFNs are similar to those of type I IFNs (Kotenko et al, 2003; Dumoutier et al, 2004). Consequently, type III and type I IFNs share many biological activities including the ability to induce an antiviral state in cells (Kotenko and Donnelly, 2006; Ank et al, 2006b). However, whereas type I IFN receptors are expressed in most cell types, IFN-λR1 demonstrates a more restricted pattern of expression, limiting the response to type III IFNs to primarily epithelial-like tissues. Therefore, although both type I and type III IFNs share similar expression pattern and biological activities, they may play distinct roles in the establishment of multifaceted antiviral response. Type III IFNs have an important physiological role in antiviral response because a recombinant VACV expressing murine type III IFN was highly attenuated in vivo in the intranasal infection model (Bartlett et al, 2005). Moreover, type III IFNs demonstrated potent antiviral activity against Herpes simplex virus (HSV)-2 in the vaginal infection model (Ank et al, 2006a). In contrast, they were inefficient in systemic infections caused by *Encephalomyocarditis virus* (EMCV) and *Lymphocytic choriomeningitis* virus (LCMV) (Ank et al, 2006a), suggesting that IFN-λs are important mediators of antiviral response in mucosal/epithelial tissues. The functional importance and uniqueness of type III IFNs for antiviral resistance needs further characterization and hitherto there were no reported virus defense mechanisms against these IFNs.

All IFNs activate Janus kinase (JAK)-Signal Transducers and Activators of Transcription (STAT) signal transduction pathway (Kotenko et al, 2004; Pestka et al, 2004). The activation of type I and type III IFN receptors, despite their differences, results in phosphorylation of Jak kinases Jak 1 and Tyk2 and this is followed by phosphorylation of STAT1 and STAT2, as well as STAT3, STAT4 and STAT5 to a lesser extent (Kotenko et al, 2003; Dumoutier et al, 2004; Kotenko et al, 2004; Pestka et al, 2004). STATs homo- or heterodimerize, translocate into the nucleus and bind to the promoter region of IFN-stimulated genes (ISGs) leading to gene transcription. STAT homo- and heterodimers bind to specific DNA elements. For instance, STAT1-STAT2 heterodimers associate with a DNA-binding protein IRF9 (p48) forming a transcriptional complex designated ISGF3 (IFN-stimulated gene factor 3), which binds to the IFN-stimulated response element (ISRE). Type II IFN activates predominately STAT1 and transcription of genes preceded by a GAS (gamma-activated sequence) element.

Type I and type III IFNs are produced and secreted in response to viral infections (Kotenko et al, 2004; Pestka et al, 2004; Ank et al, 2006b; Kotenko and Donnelly, 2006). Binding of IFNs to their corresponding cellular receptor complexes induces a signaling cascade that leads to the expression of more than 300 ISGs (Der et al, 1998; Kotenko et al, 2003; Dumoutier et al, 2004). Many ISGs encode important mediators of antiviral response such as double-stranded (ds) RNA-activated protein kinase (PKR), 2',5'-oligoadenylate synthetase (OAS) and Mx proteins (Levy and Garcia-Sastre, 2001; Kotenko et al, 2003). These antiviral mediators inhibit protein synthesis, cleave viral RNA or interfere with protein/RNA trafficking. These enzymatic activities are directed toward suppressing virus replication, making the IFN system one of the most important defense mechanisms against viral infections. In turn, viruses have developed many strategies to circumvent IFN-induced antiviral protection, generally interfering with IFN signaling.

The Poxviridae are a family of large dsDNA viruses that encode numerous immunomodulatory proteins. Vaccinia virus (VACV), the smallpox vaccine, encodes two secreted proteins that function as IFN antagonists. The B8 protein is the soluble receptor for IFN-γ (Alcami and Smith, 1995; Mossman et al, 1995), whereas the B18 protein of VACV strain Western Reserve binds IFN-α, IFN-β and IFN-ω and suppresses interaction of IFNs with their membrane-bound receptor complexes.

Many orthopoxviruses encode orthologues of B18 that are predicted to, or have been shown to, neutralize IFN-α/β. For example, Yaba-like disease virus (YLDV), a strain of Tanapoxvirus, which causes vesicular skin lesions in primates and can be transmitted to humans, encodes protein Y136 that shares 27% aa identity with B18 (Lee et al, 2001). However, the ability of Y136 to inhibit biological activities of IFNs is unknown. Similarly, the ability of poxvirus IFN-binding proteins to neutralize type III IFNs and novel members of the type I IFN family, IFN-κ and IFN-ε has not been investigated hitherto.

Figure 5:
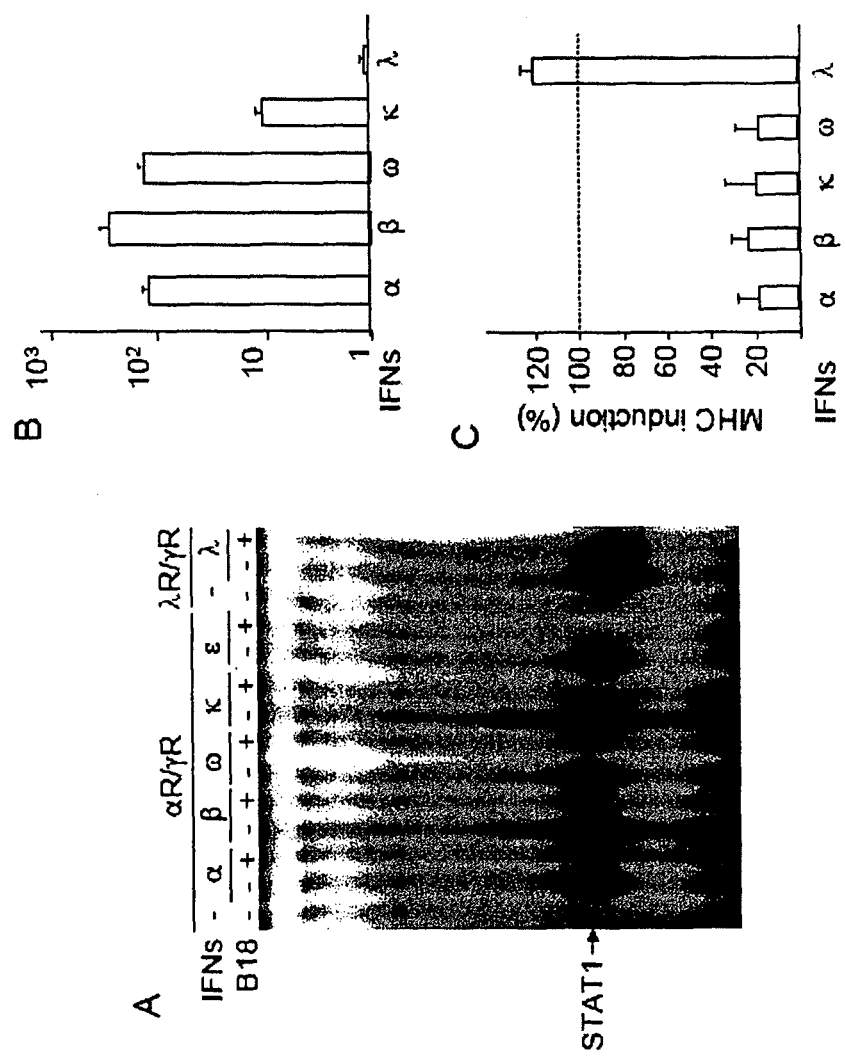
Figure 6:
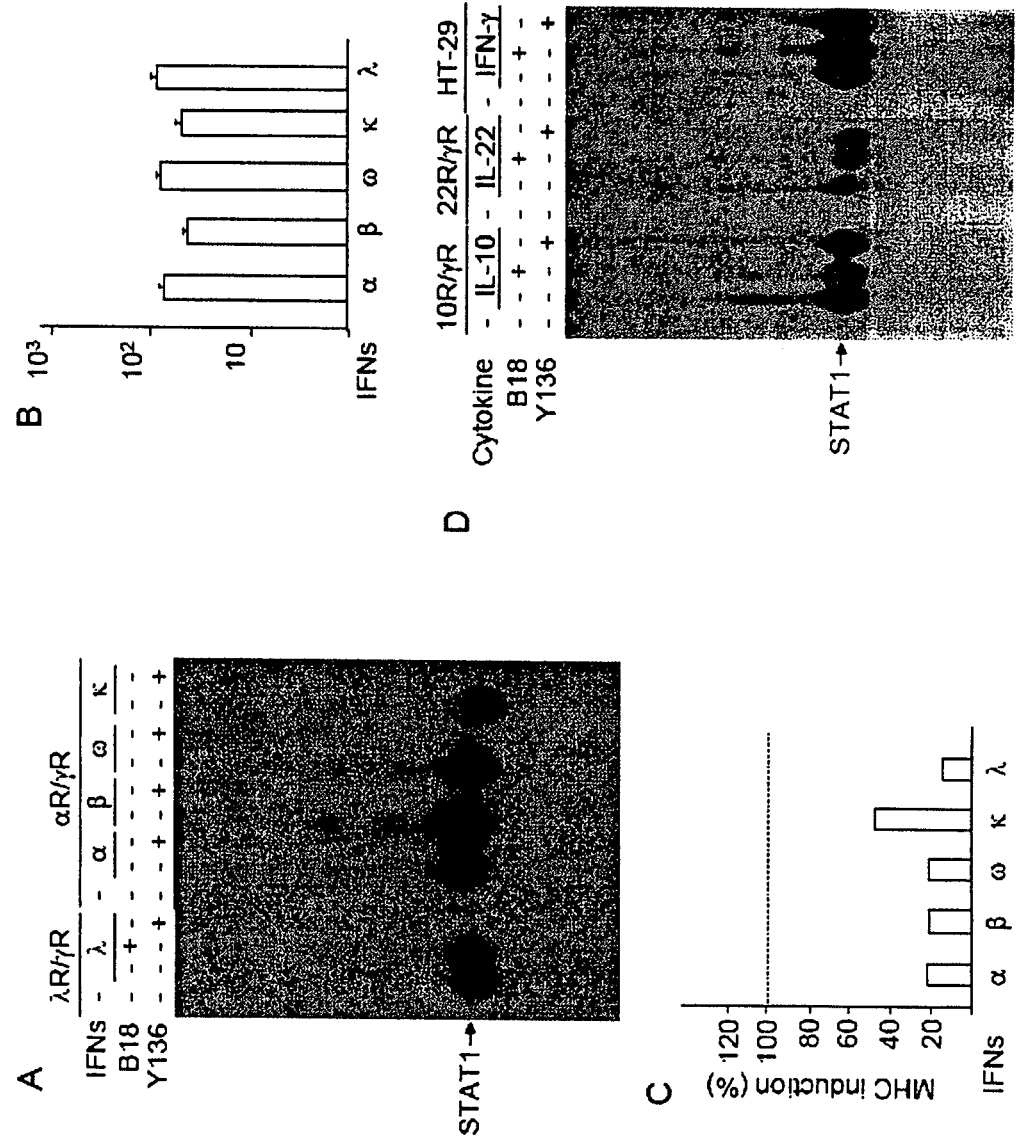

VACV B18 is shown to be a specific antagonist of all human type I IFNs. In addition to those type I IFNs investigated previously, it is demonstrated herein that B18 also inhibits the poorly characterized IFN-κ and IFN-ε (FIGS. 5-8). B18 protein binds all type I IFNs strongly (FIG. 7) and inhibits their signaling and biological activities including antiviral protection and up-regulation of MHC class I antigen expression (FIG. 5). However, B18 is unable to interact with type III IFNs and has no effect on their signaling and biological activities (FIGS. 5-8), suggesting that type III IFNs may be more potent for the treatment of certain poxvirus infections.

In contrast, the Y136 protein from YLDV not only neutralizes all human type I IFNs, but also acts as an antagonist of type III IFNs. Y136 interacts with all type I and type III IFNs and neutralizes their ability to induce signal transduction and biological activities in IFN-responsive cells (FIGS. 5-8). The ability of YLDV to inhibit type III IFNs as well as type I IFNs is interesting because infections caused by Yatapoxviruses are restricted to the dermis (Smith, 2006) where type III IFN receptors are expressed. Orthopoxviruses, in contrast, may cause systemic infections.

Figure 2:
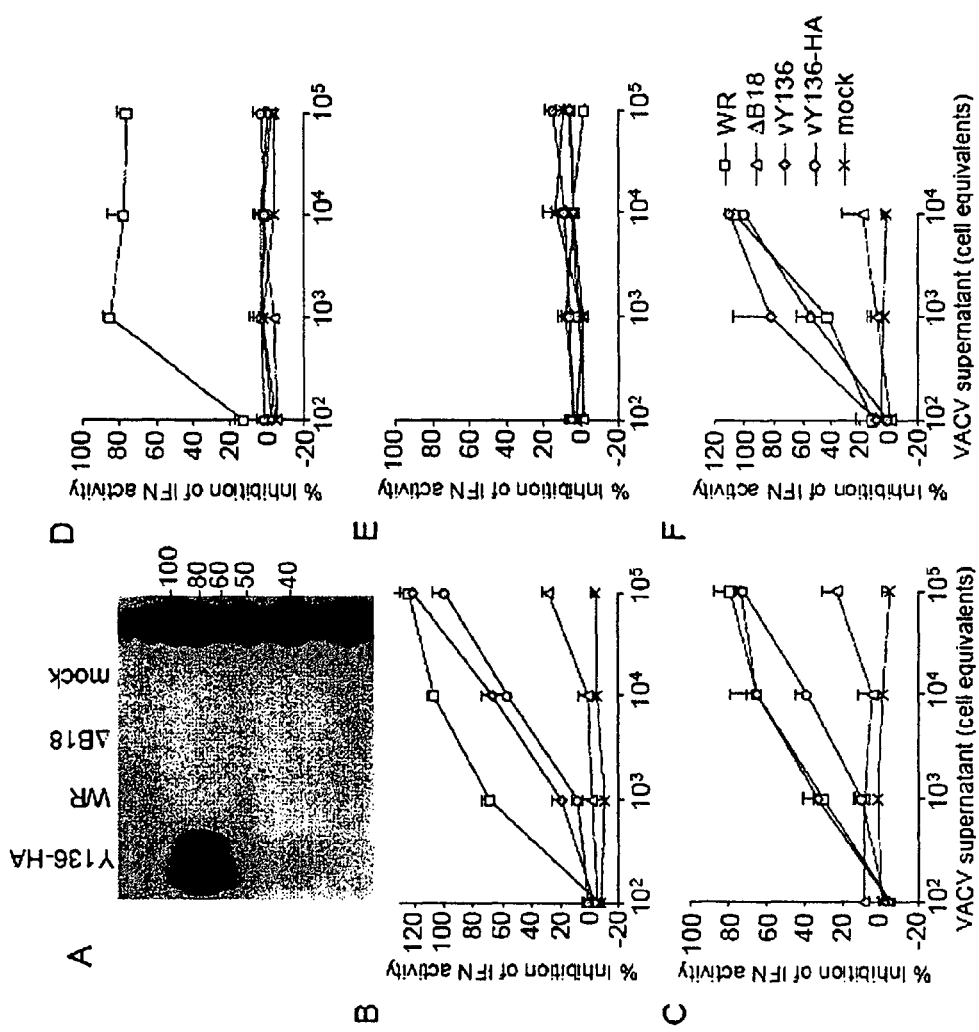

Another difference between B18 and Y136 is the species specificity of the type I IFNs that these virus proteins bind and inhibit. Whereas B18 inhibits a broad range of IFNs including mouse IFN-α, Y136 inhibits only primate and not rodent type I IFNs (FIG. 2). This specificity fits with the host range of Yatapoxviruses being restricted to primates (Smith, 2006) whereas several Orthopoxviruses, such as Ectromelia virus, Monkeypox virus, Cowpox virus and probably VACV, infect rodents (Fenner et al, 1989).

While all three types of IFNs and IL-10-related cytokines belong to the same cytokine family (CRF2 cytokine family; See FIG. 1D) and share limited primary and structural similarity (Kotenko, 2002; Kotenko et al, 2004; Langer et al, 2004), B18 and Y136 proteins did not inhibit the actions of other CRF2 cytokines, such as type II IFN (IFN-γ), IL-10 or IL-22 (FIG. 6D).

The VACV B18 protein is secreted from infected cells but is also present on the cell surface where it can protect uninfected cells from type I IFNs (Morikawa et al, 1993; Colamonici et al, 1995; Alcami et al, 2000). Similarly, cells expressing Y136 retained some of the viral protein on the cell surface (FIGS. 8B and C) and this cell surface protein still acted as efficient IFN antagonist. The ability of both viral proteins to exist as both soluble and cell surface forms provides a very effective mechanism to inhibit IFN activities in a localized infected area. Cells invaded by a virus produce type I and type III IFNs that activate neighbouring cells making these resistant to subsequent virus infection. However, cells infected with VACV or YLDV produce IFN antagonists that after release may bind to both infected and neighbouring uninfected cells to protect these from IFN. Thus virus spread is unhindered by these IFNs.

Importantly, Y136 and B18 have strong neutralizing capabilities toward IFN-β (FIG. 5B), the first IFN produced by virus-infected cells (Levy et al, 2001; Honda et al, 2005). Moreover, cells stably expressing either B18 or Y136 proteins not only fail to up-regulate MHC class I antigen expression in response to IFNs, but also down-regulate the constitutive level of MHC class I antigen expression (FIG. 8D and data not shown). While not being limited to any particular theory, the inventors hypothesize that this down-regulation is likely due to the neutralization of constitutively produced (at a low level) type I IFNs. Interestingly, the down-regulation is stronger in cells expressing Y136, suggesting that constitutively active type III IFN expression contributes to the maintenance of the basal level of MHC class I antigen expression in HT-29 cells. These results provide additional evidence that a low level of constitutive IFN expression is maintained in cells to provide "the state of readiness" to fight viral infections (Levy et al, 2001; Honda et al, 2005).

It is noteworthy that cellular type I and type III IFN receptors and viral type I and type III IFN-binding proteins belong to different receptor families and do not reveal any substantial primary sequence similarity (FIG. 1A). Both B18 and Y136 show limited aa similarity to the members of the IL-1 receptor and immunoglobulin superfamily, whereas all cellular IFN receptors as well as receptors for IL-10-related cytokines form the class II cytokine receptor family and have fibronectin like domains. Although the ligand-receptor interaction sites on either IFN or viral IFN-binding proteins remain to be characterized, it is unlikely that cellular and viral IFN receptors bind to the same IFN epitopes. It was demonstrated that at least two regions of IFN-α molecules, the C-terminal and N-terminal epitopes, are involved in interaction with B18, unlike the interaction of IFN-α with the cellular receptor (Liptakova et al, 1997). B18 demonstrated broad species specificity, binding to human, rat, mouse, bovine and rabbit type I IFNs (Symons et al, 1995), whereas cellular type I IFN receptors have restrictive species specificity.

Figure 4:
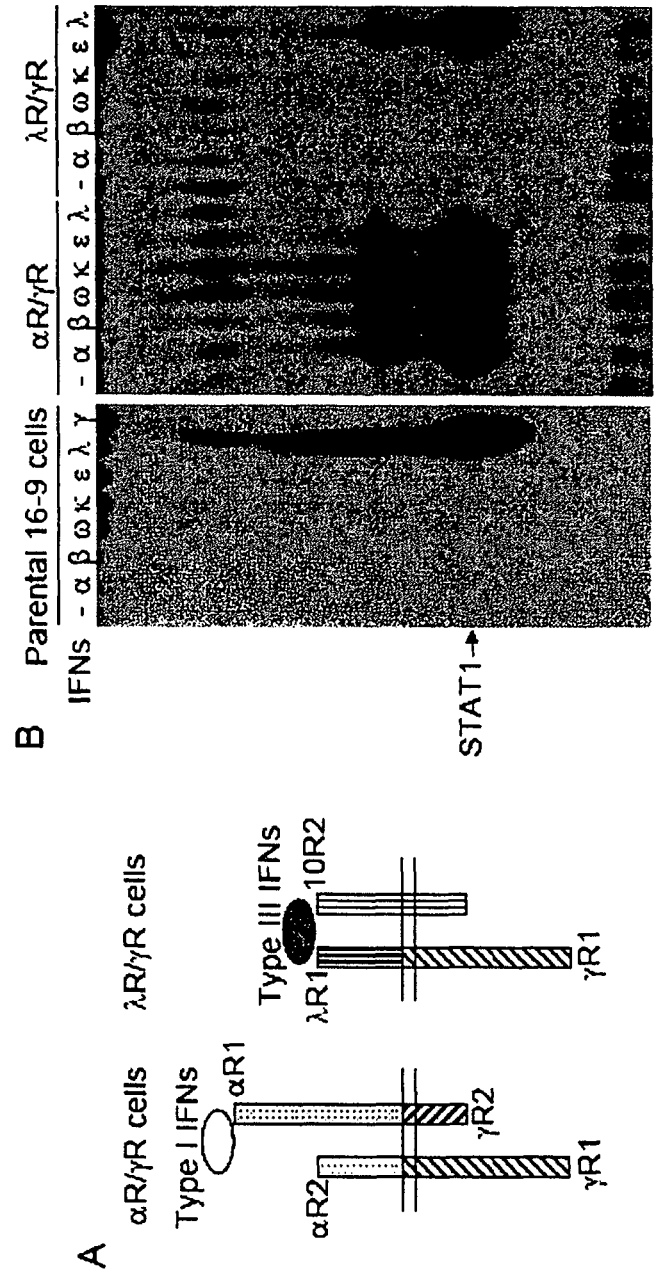

Type I and type III IFNs have low sequence identity, utilize distinct receptor complexes, and do not demonstrate any receptor binding cross-reactivity (FIG. 4B). Therefore, the fact that Y136 protein interacts with both types of IFNs in a competitive manner (FIGS. 7 and 8) strongly suggests that type I and type III IFNs possess a similar binding site(s) on their surfaces to which Y136 protein binds. Moreover, because B18 and Y136 compete for IFN binding, it is hypothesized that both viral proteins interact with the same or overlapping site(s) on the IFN molecules. In addition, the inventors hypothesize that the binding site(s) on Y136 for these different IFNs is (are) overlapping. It is interesting to speculate that these observations raise the possibility that a cellular receptor may exist that can interact with both types of IFNs through this common epitope. The existence of such a hypothetical receptor, which is likely to belong to the IL-1 receptor family, may explain why poxviruses did not utilize cellular IFN receptors to create their own IFN antagonist, but rather captured a different receptor. Nevertheless, it remains to be determined if such a cellular receptor exists.

The instant description demonstrates that the biological activities of all type I IFNs, including IFN-ω and IFN-ε, can be inhibited by both B18 and Y136 proteins. Surprisingly, Y136, but not B18, can also inhibit type III IFN-induced signaling and biological activities. Although type I and type III IFNs demonstrate only 15-20% aa identity, they compete for the same binding site on Y136. These data represent the first viral defense mechanism against type III IFNs, and its existence underscores the importance of type III IFNs for antiviral protection. These data also show that although type I and type III IFNs share many biological activities, different poxviruses have developed unique strategies to counteract them. These results also suggest that type III IFNs may be effective treatment for poxyiral infections.

As claimed and described further herein, the data presented here that expression of type III IFNs from VACV caused a dramatic reduction in virulence, suggest that type III IFNs or antagonists of Y136 and/or B18 may be potent reagents for treating some poxvirus infections. Conversely, the use of Y136 and/or B18 proteins as antagonists of IFNs of type I and III are potent reagents for the amelioration or prevention of inflammatory or detrimental immunologic conditions.

Descriptions of the molecular biological techniques useful to the practice of the invention including mutagenesis, PCR, cloning, and the like include Berger and Kimmel, GUIDE TO MOLECULAR CLONING TECHNIQUES, METHODS IN ENZYMOLOGY, volume 152, Academic Press, Inc., San Diego, Calif. (Berger); Sambrook et al., MOLECULAR CLONING—A LABORATORY MANUAL (2nd Ed.), Vol. 1-3, Cold Spring Harbor Laboratory, Cold Spring Harbor, N.Y., 1989, and CURRENT PROTOCOLS IN MOLECULAR BIOLOGY, F. M. Ausubel et al., eds., Current Protocols, a joint venture between Greene Publishing Associates, Inc. and John Wiley & Sons, Inc.; Berger, Sambrook, and Ausubel, as well as Mullis et al., U.S. Pat. No. 4,683,202 (1987); PCR PROTOCOLS A GUIDE TO METHODS AND APPLICATIONS (Innis et al. eds), Academic Press, Inc., San Diego, Calif. (1990) (Innis); Arnheim & Levinson (Oct. 1, 1990) C&EN 36-47. For suitable expression systems for both prokaryotic and eukaryotic cells see, e.g., Chapters 16 and 17 of Sambrook, et al., MOLECULAR CLONING: A LABORATORY MANUAL 2nd ed., Cold Spring Harbor Laboratory, Cold Spring Harbor Laboratory Press, Cold Spring Harbor, N.Y., 1989.

The therapeutic composition of the invention comprises, in certain embodiments, for example, an Y136 nucleic acid; a nucleic acid that binds an Y136 encoding nucleic acid; an Y136 polypeptide, peptide analog, pseudopeptide or peptidomimetic based thereon; a small molecule modulator of Y136 or a Y136 protein-protein interaction; or a Y136-specific antibody or biologically-active derivatives or fragments thereof. As described herein, Y136 is a specific antagonist of both type I and type II inteferons. Therefore, targeting the expression and/or activity of these nucleic acids, polypeptides, and homologs thereof will allow for a novel treatment of various acute and chronic diseases and conditions related to inflammation and immunity.

The therapeutic of the invention may be used in the manufacture of a medicament for treating, diagnosing or preventing disorders or syndromes including, e.g., cardiovascular disease, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, hypercoagulation, hemophilia, ulcers, wounds, lesions, cuts, abrasions, oxidative damage, age-related tissue degeneration, surgically related lesions, burns, muscle weakness, muscle atrophy, connective tissue disorders, idiopathic thrombocytopenic purpura, heart failure, secondary pathologies caused by heart failure and hypertension, hypotension, angina pectoris, myocardial infarction, tuberous sclerosis, scleroderma, transplantation, inflammation, chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.) Hyperproliferative Disorders, neoplasms, autoimmune disease, cystic fibrosis, allergic reactions and conditions, such as asthma (particularly allergic asthma) or other respiratory problems, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Autoimmune Pulmonary Inflammation, Guillain-Barre Syndrome, insulin dependent diabetes mellitis, and autoimmune inflammatory eye disease, naphylaxis, hypersensitivity to an antigenic molecule, or blood group incompatibility, graft versus host disease (GVHD), lupus erythematosus, viral/bacterial/parasitic infections, multiple sclerosis, autoimmune disease, allergies, immunodeficiencies, graft versus host disease, asthma, emphysema, ARDS, inflammation and modulation of the immune response, viral pathogenesis, aging-related disorders, Th1 inflammatory diseases such as rheumatoid arthritis, multiple sclerosis, inflammatory bowel diseases, AIDS, wound repair, heart attacks, heart failure, muscular dystrophy, bed sores, diabetic ulcers, oxidative damage, and tissue damage such as sinusitis or mucositis, wrinkles, eczema or dermatitis, dry skin, obesity, diabetes, endocrine disorders, anorexia, bulimia, renal artery stenosis, interstitial nephritis, glomerulonephritis, polycystic kidney disease, systemic, renal tubular acidosis, IgA nephropathy, nephrological disesases, hypercalceimia, Lesch-Nyhan syndrome, Von Hippel-Lindau (VHL) syndrome, trauma, regeneration (in vitro and in vivo), Hirschsprung's disease, Crohn's Disease, appendicitis, endometriosis, laryngitis, psoriasis, actinic keratosis, acne, hair growth/loss, allopecia, pigmentation disorders, myasthenia gravis, alpha-mannosidosis, beta-mannosidosis, other storage disorders, peroxisomal disorders such as zellweger syndrome, infantile refsum disease, rhizomelic chondrodysplasia (chondrodysplasia punctata, rhizomelic), and hyperpipecolic acidemia, osteoporosis, muscle disorders, urinary retention, Albright Hereditary Ostoeodystrophy, ulcers, Alzheimer's disease, stroke, Parkinson's disease, Huntington's disease, cerebral palsy, epilepsy, Lesch-Nyhan syndrome, multiple sclerosis, ataxia-telangiectasia, behavioral disorders, addiction, anxiety, pain, neuroprotection, Stroke, Aphakia, neurodegenerative disorders, neurologic disorders, developmental defects, conditions associated with the role of GRK2 in brain and in the regulation of chemokine receptors, encephalomyelitis, anxiety, schizophrenia, manic depression, delirium, dementia, severe mental retardation and dyskinesias, Gilles de la Tourette syndrome, leukodystrophies, cancers, breast cancer, CNS cancer, colon cancer, gastric cancer, lung cancer, melanoma, ovarian cancer, pancreatic cancer, kidney cancer, colon cancer, prostate cancer, neuroblastoma, and cervical cancer, Neoplasm; adenocarcinoma, lymphoma; uterus cancer, benign prostatic hypertrophy, fertility, control of growth and development/differentiation related functions such as but not limited maturation, lactation and puberty, reproductive malfunction, and/or other pathologies and disorders of the like.

In a further aspect, the invention includes a method of treating or preventing a pathological condition associated with a disorder in a mammal by administering to the subject a Y136 polypeptide, a Y136 nucleic acid, or a Y136-specific antibody to a subject (e.g., a human subject), in an amount sufficient to alleviate or prevent the pathological condition. In preferred embodiments, the disorder, includes, e.g., the diseases and disorders disclosed above and/or other pathologies and disorders of the like.

Nucleic Acids

The invention includes an isolated nucleic acid that encodes a Y136 polypeptide, or a fragment, homolog, analog, fusion protein, pseudopeptide, peptidomimetic or derivative thereof. For example, the nucleic acid can encode a polypeptide at least 30%, 40%, 50%, 60%, 70%, 80%, 90% or 100% identity to a polypeptide comprising the amino acid sequences of SEQ ID NOS: 1 or portion thereof. The nucleic acid can be, for example, a genomic DNA fragment or a cDNA molecule that includes the nucleic acid sequence of SEQ ID NOS: 2. In certain embodiments the homolgous nucleic acid has 30%, 40%, 50%, 60%, 70%, 80%, 90%, or 95% homology to a Y136 gene or portion thereof. Also included in the invention is an oligonucleotide, e.g., an oligonucleotide which includes at least 6 contiguous nucleotides of a Y136 nucleic acid (e.g., SEQ ID NOS: 2) or a complement of said oligonucleotide.

By "nucleotide" is meant a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). By "modified bases" in this aspect is meant nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N-6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra).

As used herein, "nucleic acids" or "polynucleotides" is used generically to refer to biopolymers of nucleotides or modified nucleotides, and encompasses DNA, RNA, nucleic acid analogs and derivatives, for example, peptide nucleic acids. The nucleic acid molecule may be single-stranded or double-stranded, but preferably is comprised double-stranded DNA. A polynucleotide can be a DNA molecule, a cDNA molecule, genomic DNA molecule, or an RNA molecule. A polynucleotide as DNA or RNA can include a sequence wherein T (thymidine) can also be U (uracil). If a nucleotide at a certain position of a polynucleotide is capable of forming a Watson-Crick pairing with a nucleotide at the same position in an anti-parallel DNA or RNA strand, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process.

In another embodiment, an isolated nucleic acid molecule of the invention comprises a nucleic acid molecule that is a complement of the nucleotide sequence of Y136, a Y136 binding protein, and/or a Y136 receptor. As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect.

"Complementarity" refers to the ability of a nucleic acid to form hydrogen bond(s) or hybridize with another nucleic acid sequence by either traditional Watson-Crick or other non-traditional types. As used herein "hybridization," refers to the binding, duplexing, or hybridizing of a molecule only to a particular nucleotide sequence under low, medium, or highly stringent conditions, including when that sequence is present in a complex mixture (e.g., total cellular) DNA or RNA.

"Derivatives" are compositions formed from the native compounds either directly, by modification, or by partial substitution. "Analogs" are nucleic acid sequences or amino acid sequences that have a structure similar to, but not identical to, the native compound. Derivatives or analogs of the nucleic acids or proteins of the invention include, but are not limited to, molecules comprising regions that are substantially homologous to the nucleic acids or proteins of the invention, in various embodiments, by at least about 30%, 40%, 50%, 60%, 70%, 80%, 90%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993. Nucleic acid derivatives and modifications include those obtained by gene replacement, site-specific mutation, deletion, insertion, recombination, repair, shuffling, endonuclease digestion, PCR, subcloning, and related techniques.

By "homologous" or "related" to Y136 is meant that the nucleotide sequence of two or more nucleic acid molecules is partially or completely identical, and genes encoding for proteins with similar function as Y136 and B18 proteins in various organisms, including human, rodent, primate, rabbit, pig, protozoans, fungi, plants, and other microorganisms and parasites. The equivalent RNA sequence also includes in addition to the coding region, regions such as 5'-untranslated region, 3'-untranslated region, introns, intron-exon junction and the like. Nucleic acids are homologous when they are derived, naturally or artificially, from a common ancestor sequence (e.g., orthologs or paralogs). If the homology between two nucleic acids is not expressly described, homology can be inferred by a nucleic acid comparison between two or more sequences. If the sequences demonstrate some degree of sequence similarity, for example, greater than about 30% at the primary amino acid structure level, it is concluded that they share a common ancestor. For purposes of the present invention, genes are homologous if the nucleic acid sequences are sufficiently similar to allow recombination and/or hybridization under low stringency conditions. As used herein "hybridization," refers to the binding, duplexing, or hybridizing of a molecule only to a particular nucleotide sequence under low, medium, or highly stringent conditions, including when that sequence is present in a complex mixture (e.g., total cellular) DNA or RNA.

In one embodiment, the invention encompasses compositions comprising an isolated nucleic acid encoding Y136 polypeptide (SEQ ID NO. 1) or portion thereof. In certain embodiments, the invention encompasses nucleic acids or polynucleotides encoding full-length Y136 polypeptides. In additional embodiments, the invention encompasses nucleic acids or polynucleotides encoding active polypeptide portions or fragments of Y136, for example, Y136 polypeptides comprising only the interferon binding domain. Smaller Y136 polypeptides may be desirable in certain embodiments, for example, in the administration to an intact animal, in order to reduce or ameliorate an immune response. Homologs, derivatives or analogs of the nucleic acids or proteins of the invention include, but are not limited to, molecules comprising regions that are substantially homologous to Y136 nucleic acids by at least about 30%, 40%, 50%, 60%, 70%, 80%, 90%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993. Nucleic acid derivatives and modifications include those obtained by gene replacement, site-specific mutation, deletion, insertion, recombination, repair, shuffling, endonuclease digestion, PCR, subcloning, and related techniques.

Furthermore, one of ordinary skill will recognize that mutations include the substitution, deletion or addition of polynucleotides or nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

In another aspect the invention features an expression vector comprising a nucleic acid sequence encoding at least one of the Y136 nucleic acid molecules of the invention, in a manner which allows expression of that nucleic acid molecule. The expression vector comprises in one embodiment; a) a transcription initiation region; b) a transcription termination region; c) a nucleic acid sequence encoding at least one said nucleic acid molecule; and wherein said sequence is operably linked to said initiation region and said termination region, in a manner which allows expression and/or delivery of said nucleic acid molecule. For suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

Transcription of the nucleic acid molecule sequences are driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743 7; Gao and Huang 1993, Nucleic Acids Res., 21, 2867 72; Lieber et al., 1993, Methods Enzymol., 217, 47 66; Zhou et al., 1990, Mol. Cell. Biol., 10, 4529 37). All of these references are incorporated by reference herein. Several investigators have demonstrated that nucleic acid molecules, such as ribozymes expressed from such promoters can function in mammalian cells (e.g. Kashani-Sabet et al., 1992, Antisense Res. Dev., 2, 3 15; Ojwang et al., 1992, Proc. Natl. Acad. Sci. USA, 89, 10802 6; Chen et al, 1992, Nucleic Acids Res., 20, 4581 9; Yu et al., 1993, Proc. Natl. Acad. Sci. USA, 90, 6340 4; L'Huillier et al., 1992, EMBO J., 11, 4411 8; Lisziewicz et al., 1993, Proc. Natl. Acad. Sci. U.S.A, 90, 8000 4; Thompson et al., 1995, Nucleic Acids Res., 23, 2259; Sullenger & Cech, 1993, Science, 262, 1566).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

In any of the embodiments, the nucleic acids encoding the Y136, Y136 binding protein, and/or Y136 receptor can be present as: one or more naked DNAs; one or more nucleic acids disposed in an appropriate expression vector and maintained episomally; one or more nucleic acids incorporated into the host cell's genome; a modified version of an endogenous gene encoding the components of the complex; one or more nucleic acids in combination with one or more regulatory nucleic acid sequences; or combinations thereof. The nucleic acid may optionally comprise a linker peptide or fusion protein component, for example, His-Tag, FLAG-Tag, fluorescent protein, GST, TAT, an antibody portion, a signal peptide, and the like, at the 5' end, the 3' end, or at any location within the ORF.

Host Cells

As used in herein "cell" is used in its usual biological sense, and does not refer to an entire multicellular organism. The cell can, for example, be in vivo, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified.

The term "host cell" includes a cell that might be used to carry a heterologous nucleic acid or has a disruption of an endogenous gene. The terms "host cell" and "recombinant host cell" are used interchangeably herein. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell.

Thus, in other aspects, the invention relates to a host cell expressing a recombinant Y136 transgene, and methods of making the same. The host cell may be eukaryotic or prokaryotic and expression of the recombinant Y136 protein may be transient or stable. In one embodiment, the method comprises culturing the host cell of invention (into which an exogenous nucleic acid has been introduced). The transgene can disrupt or encode a protein that is normally exogenous to the transgenic cell or animal, including a human protein. The transgene can be linked to a heterologous or a native promoter.

Another aspect of the invention pertains to host cells into which a recombinant expression vector containing a Y136 transgene of the invention has been introduced. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. In any of the embodiments, the nucleic acids can be present as: one or more naked DNAs; one or more polynucleotides or nucleic acids disposed in an appropriate expression vector and maintained episomally; one or more polynucleotides or nucleic acids incorporated into the host cell's genome; a modified version of an endogenous gene encoding the components of the complex; one or more polynucleotides or nucleic acids in combination with one or more regulatory nucleic acid sequences; or combinations thereof. The nucleic acid may optionally comprise a linker peptide or fusion protein component, for example, His-Tag, FLAG-Tag, fluorescent protein, GST, TAT, an antibody portion, a signal peptide, and the like, at the 5' end, the 3' end, or at any location within the ORF.

DNA can be introduced into prokaryotic or eukaryotic cells via conventional transformation or transfection techniques. By "transformation" or "transfection" is meant a permanent or transient genetic change induced in a cell following incorporation of new DNA (i.e., DNA exogenous to the cell). Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$, RbCl, liposome, or liposome-protein conjugate can be used. Transformation can also be performed after forming a protoplast of the host cell or by electroporation. These examples are not limiting on the present invention; numerous techniques exist for transfecting host cells that are well known by those of skill in the art and which are contemplated as being within the scope of the present invention. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The eukaryotic cell may be a yeast cell (e.g., *Saccharomyces cerevisiae*) or may be a mammalian cell, including a human cell. For long-term, high-yield production of recombinant proteins, stable expression is preferred.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the protein or can be introduced on a separate vector. Cells stably transfected with the introduced nucleic acid can be identified by drug selection (e.g., cells that have incorporated the selectable marker gene will survive, while the other cells die).

Polypeptides

In other embodiments, the invention pertains to isolated nucleic acid molecules that encode Y136 polypeptides, antibody Polypeptides, or biologically active portions thereof. The polypeptides of the complex can be formed, for example, using a peptide synthesizer according to standard methods; or by expressing each polypeptide separately in a cell or cell extract, then isolating and purifying the polypeptide. In a further aspect, the invention includes a method of producing a polypeptide by culturing a cell that includes an exogenously expressed Y136 nucleic acid, under conditions allowing for expression of the Y136 polypeptide encoded by the DNA. If desired, the Y136 polypeptide can then be recovered.

In still another aspect, the invention relates to methods for treating a detrimental immunological condition comprising administering a composition comprising an effective amount of a Y136 polypeptide to an individual in need thereof. In certain embodiments, the method comprises administering a composition comprising an effective amount of a combination of a Y136 protein and a B18 protein to an individual in need thereof.

In still another aspect, the invention relates to methods for inhibiting the activity of at least one of a type I interferon, a type III interferon or a combination of both comprising administering a composition comprising an effective amount of a Y136 polypeptide to an individual in need thereof. In certain embodiments, the method comprises administering a composition comprising an effective amount of a combination of a Y136 protein and a B18 protein to an individual in need thereof.

In further aspects, the invention relates to methods for treating a condition caused by an enhanced interferon response or exaggerated interferon release such as autoimmune diseases; acute allograft rejection; septic shock; exaggerated antiviral response induced by certain viruses or viral strains comprising administering a composition comprising an effective amount of a Y136 agonist to a subject in need thereof. In certain embodiments, the Y136 antagonist is an antibody that bind immunospecifically to an epitope of a Y136 polypeptide or portion thereof.

As used herein, "proteins" or "polypeptide" is used generically to refer to biopolymers of amino acids or amino acid derivatives and analogs and encompasses natural and recombinant proteins, polypeptides, and peptides comprising natural or synthetic amino acids comprising the full-length protein, peptide portions and fragments thereof. In addition, "proteins" encompasses Y136 peptides, fragments, fusion proteins, chimeric proteins, and the like. As used herein, "fragments" are defined as sequences of at least 6 (contiguous) nucleic acids or at least 4 (contiguous) amino acids, a length sufficient to allow for specific hybridization in the case of nucleic acids or for specific recognition of an epitope in the case of amino acids, and are at most some portion less than a full length sequence.

In a related aspect, the invention encompasses recombinant Y136 polypeptides, portions, and fragments thereof comprising one or more amino acid analogs, derivatives, mimetics, or pseudopeptides. For example, the use of Y136 pseudopeptides is useful for enhancing the protease resistance of a therapeutic peptide. In still other embodiments, the invention comprises polypeptides having from about 30% sequence homology to about 99.9% sequence homology to a full length Y136 polypeptide sequence, portion or fragment thereof.

In still other aspects, the invention encompasses an isolated Y136 fusion proteins, portions or fragments thereof. In any of the embodiments of this aspect, a Y136 fusion protein may include an amino terminal (N') fusion protein portion, a carboxy terminal (C') fusion protein portion or a combination of both an N' and C' fusion portion. In additional embodiments, the invention includes chimeric forms of Y136 proteins and chimeric forms of Y136 peptides or fragments. Potential fusion protein construction will be described in further detail but include, without limitation, for example, FLAG tags, HIS tags; fluorescent tags, for example, GFP, YFP, CFP; HIV-TAT; Myc; hemagglutinin (HA); GST; MBP; VSV; Thioredoxin; beta-Gal, and the like. As will be understood by a person of skill in the art, fusion proteins can be combined in any number of ways and combinations, which are expressly contemplated as being within the scope of the invention, and are not limited by the examples described herein.

In another aspect, the invention relates to a therapeutic composition comprising an isolated Y136 polypeptide (SEQ ID NO. 1) or a portion thereof, and a pharmaceutically acceptable carrier. In certain embodiments, the invention encompasses a therapeutic composition for treating a detrimental immunological condition comprising an isolated Y136 polypeptide. In certain embodiments, the therapeutic composition further comprises a B18 polypeptide from Vaccinia virus (VACV). In still another aspect the invention relates to a therapeutic composition comprising a fusion protein comprising a first polypeptide portion consisting of SEQ ID NO. 1 or a portion thereof, and a second polypeptide portion consisting of SEQ ID NO. 5.

In another aspect, the invention includes a method of detecting the presence of a Y136 polypeptide in a sample. In the method, a sample is contacted with a compound that selectively binds to the polypeptide under conditions allowing for formation of a complex between the polypeptide and the compound. The complex is detected, if present, thereby identifying the Y136 polypeptide within the sample.

Enzymatic Nucleic Acids

By "enzymatic nucleic acid molecule" it is meant a nucleic acid molecule which has complementarity in a substrate binding region to a specified gene target, and also has or mediates an enzymatic activity which is active to specifically cleave target RNA. That is, the enzymatic nucleic acid molecule is able to intermolecularly cleave RNA, alone or as a component of an enzymatic complex, and thereby inactivate a target RNA molecule. These complementary regions allow sufficient hybridization of the enzymatic nucleic acid molecule to the target RNA and thus permit cleavage. One hundred percent complementarity is preferred, but complementarity as low as 50-75% can also be useful in this invention (see for example Werner and Uhlenbeck, 1995, Nucleic Acids Research, 23, 2092 2096; Hammann et al., 1999, Antisense and Nucleic Acid Drug Dev., 9, 25 31). The nucleic acids can be modified at the base, sugar, and/or phosphate groups. The term "enzymatic nucleic acid" is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, siRNA, micro RNA, short hairpin RNA, endoribonuclease, RNA-induced silencing complexes, endonuclease, minizyme, leadzyme, oligozyme or DNA enzyme. All of these terminologies describe nucleic acid molecules with enzymatic activity.

By "down-regulate" it is meant that the expression of the gene, or level of RNAs or equivalent RNAs encoding one or more Y136 proteins, or activity of one or more proteins, is reduced below that observed in the absence of the nucleic acid molecules of the invention. In one embodiment, inhibition or down-regulation with enzymatic nucleic acid molecule preferably is below that level observed in the presence of an enzymatically inactive or attenuated molecule that is able to bind to the same site on the target RNA, but is unable to cleave that RNA. In another embodiment, inhibition or down-regulation with antisense oligonucleotides is preferably below that level observed in the presence of, for example, an oligonucleotide with scrambled sequence or with mismatches. In another embodiment, inhibition or down-regulation of Y136 proteins, Y136 genes with the nucleic acid molecule of the instant invention is greater in the presence of the nucleic acid molecule than in its absence.

By "up-regulate" is meant that the expression of the gene, or level of RNAs or equivalent RNAs encoding one or more protein subunits, or activity of one or more protein subunits, such as Y136 proteins, and Y136 genes, is greater than that observed in the absence of the nucleic acid molecules of the invention. For example, the expression of a gene, such as Y136 proteins, and Y136 genes, can be increased in order to treat, prevent, ameliorate, or modulate a pathological condition caused or exacerbated by an absence or low level of gene expression. In one embodiment the invention relates to a method for treating or preventing bladder over activity by up-regulating the expression, release, and/or activity of a Y136 proteins, and Y136 genes.

The enzymatic nature of an enzymatic nucleic acid molecule can allow the concentration of enzymatic nucleic acid molecule necessary to affect a therapeutic treatment to be lower. This reflects the ability of the enzymatic nucleic acid molecule to act enzymatically. Thus, a single enzymatic nucleic acid molecule is able to cleave many molecules of target RNA. In addition, the enzymatic nucleic acid molecule is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to greatly attenuate the catalytic activity of a enzymatic nucleic acid molecule. Such enzymatic nucleic acid molecules can be targeted to virtually any RNA transcript, and achieve efficient cleavage in vitro (Zaug et al., 324, Nature 429 1986; Uhlenbeck, 1987 Nature 328, 596; Kim et al., 84 Proc. Natl. Acad. Sci. USA 8788, 1987; Dreyfus, 1988, Einstein Quart. J. Bio. Med., 6, 92; Haseloff and Gerlach, 334 Nature 585, 1988; Cech, 260 JAMA 3030, 1988; and Jefferies et al., 17 Nucleic Acids Research 1371, 1989; Santoro et al., 1997 supra).

The invention provides a method for producing a class of nucleic acid-based gene modulating agents which exhibit a high degree of specificity for the RNA of a desired target. For example, the enzymatic nucleic acid molecule is preferably targeted to a highly conserved sequence region of target RNAs encoding a Y136 or B18 gene such that specific treatment can be provided with either one or several nucleic acid molecules of the invention. Such nucleic acid molecules can be delivered exogenously to specific tissue or cellular targets as required. Alternatively, the nucleic acid molecules (e.g., ribozymes and antisense) can be expressed from DNA and/or RNA vectors that are delivered to specific cells.

In another embodiment, the invention features an enzymatic nucleic acid molecule having enzymatic activity to cleave an RNA or DNA molecule. In another embodiment, a nucleic acid molecule of the invention has an endonuclease activity or is a component of a nuclease complex, and cleaves RNA having a Y136 nucleic acid sequence. The nucleic acid molecules of the present invention can be modified extensively to enhance stability by modification with nuclease resistant groups, for example, 2'-amino, 2'-C-allyl, 2'-fluoro, 2'-β-methyl, 2'-H (for a review see Usman and Cedergren, 1992, TIBS 17, 34; Usman et al., 1994, Nucleic Acids Symp. Ser. 31, 163). While chemical modification of oligonucleotide internucleotide linkages with phosphorothioate, phosphorothioate, and/or 5'-methylphosphonate linkages improves stability, too many of these modifications can cause some toxicity. Therefore when designing nucleic acid molecules the amount of these internucleotide linkages should be minimized. The reduction in the concentration of these linkages should lower toxicity resulting in increased efficacy and higher specificity of these molecules.

The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., 1988, 260 JAMA 3030).

Several varieties of enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets. Thus, a single ribozyme molecule is able to cleave many molecules of target RNA. In addition, the ribozyme is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

Long double-stranded RNAs (dsRNAs; typically >200 nt) can be used to silence the expression of target genes in a variety of organisms and cell types (e.g., worms, fruit flies, and plants). Upon introduction, the long dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effecter step). Cleavage of cognate RNA takes place near the middle of the region bound by the siRNA strand. In mammalian cells, introduction of long dsRNA (>30 nt) initiates a potent antiviral response, exemplified by nonspecific inhibition of protein synthesis and RNA degradation. The mammalian antiviral response can be bypassed, however, by the introduction or expression of siRNAs.

By "double stranded RNA" or "dsRNA" is meant a double stranded RNA that matches a predetermined gene sequence that is capable of activating cellular enzymes that degrade the corresponding messenger RNA transcripts of the gene. These dsRNAs are referred to as short intervening RNA (siRNA) and can be used to inhibit gene expression (see for example Elbashir et al., 2001, Nature, 411, 494-498; and Bass, 2001, Nature, 411, 428-429). The term "double stranded RNA" or "dsRNA" as used herein refers to a double stranded RNA molecule capable of RNA interference "RNAi", including short interfering RNA "siRNA" see for example Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914. The use of inhibitory RNA molecules and techniques are known in the art and are described in detail in U.S. Pat. No. 7,022,828, the teachings of which are incorporated herein by reference in their entirety for all purposes.

Nucleic acid molecules having chemical modifications that maintain or enhance activity are provided. Such nucleic acid is also generally more resistant to nucleases than unmodified nucleic acid. Nucleic acid molecules are preferably resistant to nucleases in order to function as effective intracellular therapeutic agents. Improvements in the chemical synthesis of RNA and DNA (Wincott et al., 1995 Nucleic Acids Res. 23, 2677; Caruthers et al., 1992, Methods in Enzymology 211, 3-19 (incorporated by reference herein) have expanded the ability to modify nucleic acid molecules by introducing nucleotide modifications to enhance their nuclease stability as described above. The use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules and/or other chemical or biological molecules). The treatment of subjects with nucleic acid molecules can also include combinations of different types of nucleic acid molecules.

In one embodiment, nucleic acid catalysts having chemical modifications that maintain or enhance enzymatic activity are provided. Such nucleic acids are also generally more resistant to nucleases than unmodified nucleic acid. In another embodiment, the invention features modified enzymatic nucleic acid molecules with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, Nucleic Acid Analogues: Synthesis and Properties, in Modern Synthetic Methods, VCH, 331 417, and Mesmaeker et al., 1994, Novel Backbone Replacements for Oligonucleotides, in Carbohydrate Modifications in Antisense Research, ACS, 24 39. These references are hereby incorporated by reference herein. Various modifications to nucleic acid (e.g., antisense and ribozyme) structure can be made to enhance the utility of these molecules. For example, such modifications can enhance shelf-life, half-life in vitro, bioavailability, stability, and ease of introduction of such oligonucleotides to the target site, including e.g., enhancing penetration of cellular membranes and conferring the ability to recognize and bind to targeted cells.

Administration of Nucleic Acid Molecules. Methods for the delivery of nucleic acid molecules are described in Akhtar et al., 1992, Trends Cell Bio., 2, 139; and Delivery Strategies for Antisense Oligonucleotide Therapeutics, ed. Akhtar, 1995 which are both incorporated herein by reference. Sullivan et al., PCT WO 94/02595, further describes the general methods for delivery of enzymatic RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by a incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. For a comprehensive review on drug delivery strategies including CNS delivery, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400.

In a further embodiment, the described nucleic acid molecules, such as antisense or ribozymes, can be used in combination with other known treatments to treat conditions or diseases discussed above. For example, the described molecules can be used in combination with one or more known therapeutic agents. The molecules of the instant invention can be used as pharmaceutical agents. Pharmaceutical agents prevent, inhibit the occurrence, or treat (alleviate a symptom to some extent, preferably all of the symptoms) a disease state in a subject.

Because of their sequence specificity, trans-cleaving enzymatic nucleic acid molecules can be used as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional and abrogates protein expression from that RNA. In this manner, synthesis of a protein associated with a disease state can be selectively inhibited (Warashina et al., 1999, Chemistry and Biology, 6, 237-250).

Enzymatic nucleic acid molecules of the invention that are allosterically regulated ("allozymes") can be used to modulate Y136 or B18 gene expression. These allosteric enzymatic nucleic acids or allozymes (see for example George et al, U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842) are designed to respond to a signaling agent, which in turn modulates the activity of the enzymatic nucleic acid molecule and modulates expression of Y136 or B18 genes. In response to interaction with a predetermined signaling agent, the allosteric enzymatic nucleic acid molecule's activity is activated or inhibited such that the expression of a particular target is selectively down-regulated.

In one embodiment, the invention features modified enzymatic nucleic acid molecules with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, Nucleic Acid Analogues: Synthesis and Properties, in Modern Synthetic Methods, VCH, 331 417, and Mesmaeker et al., 1994, Novel Backbone Replacements for Oligonucleotides, in Carbohydrate Modifications in Antisense Research, ACS, 24 39. These references are hereby incorporated by reference herein. Various modifications to nucleic acid (e.g., antisense and ribozyme) structure can be made to enhance the utility of these molecules. For example, such modifications can enhance shelf-life, half-life in vitro, bioavailability, stability, and ease of introduction of such oligonucleotides to the target site, including e.g., enhancing penetration of cellular membranes and conferring the ability to recognize and bind to targeted cells.

Some vectors have been engineered to express small hairpin RNAs (shRNAs), which get processed in vivo into siRNAs-like molecules capable of carrying out gene-specific silencing. The vectors contain the shRNA sequence between a polymerase III (pol III) promoter (e.g., U6 or H1 promoters) and a 4-5 thymidine transcription termination site. The transcript is terminated at position 2 of the termination site (pol III transcripts naturally lack poly(A) tails) and then folds into a stem-loop structure with 3' UU-overhangs. The ends of the shRNAs are processed in vivo, converting the shRNAs into ~21 nt siRNA-like molecules, which in turn initiate RNAi. This latter finding correlates with recent experiments in *C. elegans, Drosophila*, plants and Trypanosomes, where RNAi has been induced by an RNA molecule that folds into a stem-loop structure.

In another aspect of the invention, enzymatic nucleic acid molecules or antisense molecules that interact with target RNA molecules, and down-regulate Y136 or B18 genes, or Y136 or B18 binding protein genes are expressed from transcription units inserted into DNA or RNA vectors. The recombinant vectors are preferably DNA plasmids or viral vectors. The use of RNAi vectors and expression systems is known and are commercially available from Ambion, Inc. (Austin, Tex.), Lentigen, Inc. (Baltimore, Md.), Panomics (Fremont, Calif.), Open Biosystems (e.g., Expression Arrest™; Huntsville, Ala.), and Sigma-Aldrich (ST. Louis, Mo.).

Enzymatic nucleic acid molecule or antisense expressing viral vectors can be constructed based on, but not limited to, lenti virus, cytomegalovirus, adeno-associated virus, retrovirus, adenovirus, or alphavirus. Preferably, the recombinant vectors capable of expressing the enzymatic nucleic acid molecules or antisense are delivered, and persist in target cells. Alternatively, viral vectors can be used that provide for expression of enzymatic nucleic acid molecules or antisense. Such vectors can be repeatedly administered as necessary. Once expressed, the enzymatic nucleic acid molecules or antisense bind to the target RNA and down-regulate its function or expression. Delivery of enzymatic nucleic acid molecule or antisense expressing vectors can be systemic, such as by intravenous or intramuscular administration, by administration to target cells explanted from the patient or subject followed by reintroduction into the patient or subject, or by any other means that would allow for introduction into the desired target cell. Antisense DNA can be expressed via the use of a single stranded DNA intracellular expression vector.

The nucleic acid molecules of the instant invention, individually, or in combination or in conjunction with other drugs, can be used to modify the expression of Y136 or B18 genes. The use of specially designed vector constructs for inducing RNA interference has numerous advantages over oligonucleotide-based techniques. The most significant advantages are stability, and induced transcription via inducible promoters. Promoter regions in the vector ensure that shRNA transcripts are constantly expressed, maintaining cellular levels at all times. Thus, the duration of the effect is not as transient as with injected RNA, which usually lasts no longer than a few days. And by using expression constructs instead of oligo injection, it is possible to perform multi-generational studies of gene knockdown because the vector can become a permanent fixture in the cell line.

By "triplex forming oligonucleotides" or "triplex oligonucleotide" is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504; Fox, 2000, Curr. Med. Chem., 7, 17-37; Praseuth et. al., 2000, Biochim. Biophys. Acta, 1489, 181-206).

In one embodiment of the enzymatic nucleic acid of the invention, a nucleic acid molecule of the instant invention can be between about 10 and 100 nucleotides in length. For example, RNAi nucleic acid molecules of the invention are preferably between about 15 and 50 nucleotides in length, more preferably between about 25 and 40 nucleotides in length (for example see Jarvis et al., 1996, J. Biol. Chem., 271, 29107 29112). Exemplary inhibitory RNA molecules of the invention are preferably between about 15 and 75 nucleotides in length, more preferably between about 20 and 35 nucleotides in length (see for example Woolf et al., 1992, PNAS., 89, 7305 7309; Milner et al., 1997, Nature Biotechnology, 15, 537 541). Exemplary triplex forming oligonucleotide molecules of the invention are preferably between about 10 and 40 nucleotides in length, more preferably between about 12 and 25 nucleotides in length (see for example Maher et al, 1990, Biochemistry, 29, 8820 8826; Strobel and Dervan, 1990, Science, 249, 73 75). Those skilled in the art will recognize that all that is required is that the nucleic acid molecule be of sufficient length and suitable conformation for the nucleic acid molecule to interact with its target and/or catalyze a reaction contemplated herein. The length of the nucleic acid molecules of the instant invention are not limiting within the general limits stated. Preferably, a nucleic acid molecule that modulates, for example, down-regulates Y136 or B18 gene expression comprises between 12 and 100 bases complementary to a RNA molecule of a Y136 or B18 gene, or Y136 or B18 binding protein gene.

Antisense

Also included in the invention are antisense oligonucleotides derived from a Y136 nucleic acid sequence (SEQ ID NO. 2). By "antisense nucleic acid", it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop or hairpin, and/or an antisense molecule can bind such that the antisense molecule forms a loop or hairpin. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol, 40, 1-49, which are incorporated herein by reference in their entirety. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

In addition, binding of single stranded DNA to RNA can result in nuclease degradation of the heteroduplex (Wu-Pong, supra; Crooke, supra). To date, the only backbone modified DNA chemistry which acts as substrates for RNase H are phosphorothioates, phosphorodithioates, and borontrifluoridates. Recently it has been reported that 2'-arabino and 2'-fluoro-arabino-containing oligos can also activate RNase H activity. A number of antisense molecules have been described that utilize novel configurations of chemically modified nucleotides, secondary structure, and/or RNase H substrate domains (Woolf et al., International PCT Publication No. WO 98/13526; Thompson et al., International PCT Publication No. WO 99/54459; Hartmann et al., U.S. Ser. No. 60/101,174 which was filed on Sep. 21, 1998) all of these are incorporated by reference herein in their entirety.

Oligonucleotides (eg; antisense, GeneBlocs) are synthesized using protocols known in the art as described in Caruthers et al., 1992, Methods in Enzymology 211, 3 19, Thompson et al., International PCT Publication No. WO 99/54459, Wincott et al., 1995, Nucleic Acids Res. 23, 2677 2684, Wincott et al., 1997, Methods Mol. Bio., 74, 59, Brennan et al, 1998, Biotechnol Bioeng., 61, 33 45, and Brennan, U.S. Pat. No. 6,001,311. All of these references are incorporated herein by reference. In a non-limiting example, small scale syntheses are conducted on a 394 Applied Biosystems, Inc. synthesizer. Alternatively, the nucleic acid molecules of the present invention can be synthesized separately and joined together post-synthetically, for example by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204).

Methods for the delivery of nucleic acid molecules are described in Akhtar et al., 1992, Trends Cell Bio., 2, 139; and Delivery Strategies for Antisense Oligonucleotide Therapeutics, ed. Akhtar, 1995 which are both incorporated herein by reference. Sullivan et al., PCT WO 94/02595, further describes the general methods for delivery of enzymatic RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by a incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. For a comprehensive review on drug delivery strategies including CNS delivery, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400.

Injection and transfection of dsRNA into cells and organisms has been the main method of delivery of siRNA. And while the silencing effect lasts for several days and does appear to be transferred to daughter cells, it does eventually diminish. Recently, however, a number of groups have developed expression vectors to continually express siRNAs in transiently and stably transfected mammalian cells. (See, e.g., Brummelkamp T R, Bernards R, and Agami R. (2002). A system for stable expression of short interfering RNAs in mammalian cells. Science 296:550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20:500-505; Miyagishi M, and Taira K. (2002). U6-promoter-driven siRNAs with four uridine 3' overhangs efficiently suppress targeted gene expression in mammalian cells. Nature Biotechnol. 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16:948-958; Paul C P, Good P D, Winer I, and Engelke D R. (2002). Effective expression of small interfering RNA in human cells. Nature Biotechnol. 20:505-508; Sui G, Soohoo C, Affar E-B, Gay F, Shi Y, Forrester W C, and Shi Y. (2002). A DNA vector-based RNAi technology to suppress gene expression in mammalian cells. Proc. Natl. Acad. Sci. USA 99(6):5515-5520; Yu J-Y, DeRuiter S L, and Turner D L. (2002). RNA interference by expression of short-interfering RNAs and hairpin RNAs in mammalian cells. Proc. Natl. Acad. Sci. USA 99(9):6047-6052, which are herein incorporated by reference in their entirety).

Antibodies

In one aspect, the invention relates to an agent capable of binding immunospecifically to a Y136 polypeptide, for example, an antibody. The term "antibody" as used herein refers to immunoglobulin molecules and immunologically active portions of immunoglobulin (Ig) molecules, i.e., molecules that contain an antigen-binding site that specifically binds (immunoreacts with) an antigen, comprising at least one, and preferably two, heavy (H) chain variable regions (abbreviated herein as VH), and at least one and preferably two light (L) chain variable regions (abbreviated herein as VL). Such antibodies include, but are not limited to, polyclonal, monoclonal, chimeric, single chain, Fab, Fab' and F(ab')$_2$ fragments, and an Fab expression library.

The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4. In general, antibody molecules obtained from humans relates to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain. Reference herein to antibodies includes a reference to all such classes, subclasses and types of human antibody species.

Antibodies can be prepared from the intact polypeptide or fragments containing peptides of interest as the immunizing agent. A preferred antigenic polypeptide fragment is 15-100 contiguous amino acids of Y136. In one embodiment, the peptide is located in a non-transmembrane domain of the polypeptide, e.g., in an extracellular or intracellular domain. An exemplary antibody or antibody fragment binds to an epitope that is accessible from the extracellular milieu and that alters the functionality of the protein. In certain embodiments, the present invention comprises antibodies that recognize and are specific for one or more epitopes of a Y136 protein, variants, portions and/or combinations thereof. In alternative embodiments antibodies of the invention may target and interfere with the Y136/IFN interaction to inhibit signaling.

The preparation of monoclonal antibodies is well known in the art; see for example, Harlow et al., Antibodies: A Laboratory Manual, page 726 (Cold Spring Harbor Pub. 1988). Monoclonal antibodies can be obtained by injecting mice or rabbits with a composition comprising an antigen, verifying the presence of antibody production by removing a serum sample, removing the spleen to obtain B lymphocytes, fusing the lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by techniques well known in the art.

In other embodiments, the antibody can be recombinantly produced, e.g., produced by phage display or by combinatorial methods. Phage display and combinatorial methods can be used to isolate recombinant antibodies that bind to Y136, Y136 binding proteins, and/or Y136 receptor proteins or fragments thereof (as described in, e.g., Ladner et al. U.S. Pat. No. 5,223,409; Fuchs et al. (1991) Bio/Technology 9:1370-1372; Hay et al. (1992) Hum Antibod Hybridomas 3:81-85; Huse et al. (1989) Science 246:1275-1281; Clackson et al. (1991) Nature 352:624-628; Gram et al. (1992) PNAS 89:3576-3580.

Human monoclonal antibodies can also be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855).

A therapeutically useful antibody to the components of the complex of the invention or the complex itself may be derived from a "humanized" monoclonal antibody. Humanized monoclonal antibodies are produced by transferring mouse complementarity determining regions from heavy and light variable chains of the mouse immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found in Jones et al., *Nature* 321: 522, 1986 and Singer et al., *J. Immunol.* 150: 2844, 1993. The antibodies can also be derived from human antibody fragments isolated from a combinatorial immunoglobulin library; see, for example, Barbas et al., Methods: A Companion to Methods in Enzymology 2, 119, 1991. In addition, chimeric antibodies can be obtained by splicing the genes from a mouse antibody molecule with appropriate antigen specificity together with genes from a human antibody molecule of appropriate biological specificity; see, for example, Takeda et al., *Nature* 314: 544-546, 1985. A chimeric antibody is one in which different portions are derived from different animal species.

Anti-idiotype technology can be used to produce monoclonal antibodies that mimic an epitope. An anti-idiotypic monoclonal antibody made to a first monoclonal antibody will have a binding domain in the hypervariable region that is the "image" of the epitope bound by the first monoclonal antibody. Alternatively, techniques used to produce single chain antibodies can be used to produce single chain antibodies. Single chain antibodies are formed by linking the heavy and light chain fragments of the Fv region via an amino acid bridge, resulting in a single chain polypeptide. Antibody fragments that recognize specific epitopes, e.g., extracellular epitopes, can be generated by techniques well known in the art. Such fragments include Fab fragments produced by proteolytic digestion, and Fab fragments generated by reducing disulfide bridges. When used for immunotherapy, the monoclonal antibodies, fragments thereof, or both may be unlabelled or labeled with a therapeutic agent. These agents can be coupled directly or indirectly to the monoclonal antibody by techniques well known in the art, and include such agents as drugs, radioisotopes, lectins and toxins.

The dosage ranges for the administration of monoclonal antibodies are large enough to produce the desired effect, and will vary with age, condition, weight, sex, age and the extent of the condition to be treated, and can readily be determined by one skilled in the art. Dosages can be about 0.1 mg/kg to about 2000 mg/kg. The monoclonal antibodies can be administered intravenously, intraperitoneally, intramuscularly, and/or subcutaneously.

In certain embodiments of the invention, at least one epitope encompassed by the antigenic peptide is a region of Y136 that is located on the surface of the protein, e.g., a hydrophilic region. A hydrophobicity analysis of the protein sequence will indicate which regions of a polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824-3828; Kyte and Doolittle 1982, *J. Mol. Biol.* 157: 105-142, each incorporated herein by reference in their entirety. Antibodies that are specific for one or more domains within an antigenic protein, or derivatives, fragments, analogs or homologs thereof, are also provided herein. A protein of the invention, or a derivative, fragment, analog, homolog or ortholog thereof, may be utilized as an immunogen in the generation of antibodies that immunospecifically bind these protein components.

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, *J. Mol. Biol.* 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology*, 10:779-783 (1992)); Lonberg et al. (*Nature*, 368: 856-859 (1994)); Morrison (*Nature*, 368:812-13 (1994)); Fishwild et al, (*Nature Biotechnology*, 14:845-51 (1996)); Neuberger (*Nature Biotechnology*, 14:826 (1996)); and Lonberg and Huszar (*Intern. Rev. Immunol.*, 13:65-93 (1995)).

Human antibodies may additionally be produced using transgenic nonhuman animals which are modified so as to produce fully human antibodies rather than the animal's endogenous antibodies in response to challenge by an antigen. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the XENOMOUSE® as disclosed in PCT publications WO 96/33735 and WO 96/34096.

Fab Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., *Science* 246:1275-1281 (1989)) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an F(ab')2 fragment produced by pepsin digestion of an antibody molecule; (ii) an Fab fragment generated by reducing the disulfide bridges of an F(ab')2 fragment; (iii) an Fab fragment generated by the treatment of the antibody molecule with papain and a reducing agent and (iv) Fv fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit. Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537-539 (1983)). Because of the random assortment of immunoglobulin heavy and light chains, these hybridomas (quadromas) produce a potential mixture of ten different antibody molecules, of which only one has the correct bispecific structure. Similar procedures are disclosed in WO 93/08829, published May 13, 1993, and Traunecker et al., *EMBO J.*, 10:3655-3659 (1991).

Antibody variable domains with the desired binding specificities (antibody-antigen combining sites) can be fused to immunoglobulin constant domain sequences. For further details of generating bispecific antibodies see, for example, Suresh et al., *Methods in Enzymology*, 121:210 (1986); and Brennan et al., *Science* 229:81 (1985). Additionally, Fab' fragments can be directly recovered from *E. coli* and chemically coupled to form bispecific antibodies. Shalaby et al., *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The "diabody" technology described by Hollinger et al., *Proc. Natl. Acad. Sci. USA* 90:6444-6448 (1993) has provided an alternative mechanism for making bispecific antibody fragments. Another strategy for making bispecific antibody fragments by the use of single-chain Fv (sFv) dimers has also been reported. See, Gruber et al., *J. Immunol.* 152:5368 (1994). Antibodies with more than two valencies are contemplated. For example, trispecific antibodies can be prepared. Tutt et al., *J. Immunol.* 147:60 (1991). Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA.

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Immunoconjugates

The invention also pertains to immunoconjugates comprising an antibody conjugated to a chemical agent, or a radioactive isotope (i.e., a radioconjugate). Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Immunoliposomes

The antibodies disclosed herein can also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide-interchange reaction.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 500 mg/kg body weight. Common dosing frequencies may range, for example, from twice daily to once a week.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

Diagnostics

The description of the various aspects and embodiments is provided with reference to the exemplary Y136 genes. However, the various aspects and embodiments are also directed to genes which encode homologs, orthologs, and paralogs of other Y136 proteins and includes all isoforms, splice variants, and polymorphisms. Thus, the inhibition and the effects of such inhibition of the other genes can be performed as described herein.

In certain aspects, the invention relates to diagnostic oligonucleotides and diagnostic oligonucleotide set(s), for which a correlation exists between the health status of an individual, and the individual's expression of RNA or protein products corresponding to the nucleotide sequence. In some instances, only one oligonucleotide is necessary for such detection. Members of a diagnostic oligonucleotide set may be identified by any means capable of detecting expression or a polymorphism of RNA or protein products, including but not limited to differential expression screening, PCR, RT-PCR, SAGE analysis, high-throughput sequencing, microarrays, liquid or other arrays, protein-based methods (e.g., western blotting, proteomics, mass-spectrometry, and other methods described herein), and data mining methods, as further described herein.

In another aspect, the invention relates to a method for diagnosing or monitoring a viral disease or progression comprising detecting for the presence of the expression level of a Y136 gene or protein or both. As used herein, "gene" or "structural gene" includes the 5' UTR, 3' UTR, promoter sequences, enhancer sequences, intronic and exonic DNA of the MIF gene as well as the MIF gene mRNA or cDNA sequence.

Also included in the invention is a method of detecting the presence of a Y136 nucleic acid molecule in a sample by contacting the sample with a Y136 nucleic acid probe or primer, and detecting whether the nucleic acid probe or primer bound to a Y136 nucleic acid molecule in the sample.

In a further aspect, the invention provides a method for modulating the activity of a Y136 polypeptide by contacting a cell sample that includes the Y136 polypeptide with a compound that binds to the Y136 polypeptide in an amount sufficient to modulate the activity of said polypeptide. The compound can be, e.g., a small molecule, such as a nucleic acid, peptide, polypeptide, antibody, peptidomimetic, carbohydrate, lipid or other organic (carbon containing) or inorganic molecule, as further described herein.

For example, the compositions of the present invention will have efficacy for treatment of patients suffering from the diseases and disorders disclosed above and/or other pathologies and disorders of the like. The polypeptides can be used as immunogens to produce antibodies specific for the invention, and as vaccines. They can also be used to screen for potential agonist and antagonist compounds. In addition, a cDNA encoding Y136 may be useful in gene therapy, and Y136 may be useful when administered to a subject in need thereof. By way of non-limiting example, the compositions of the present invention will have efficacy for treatment of patients suffering from the diseases and disorders disclosed above and/or other pathologies and disorders of the like.

The invention further includes a method for screening for a modulator of disorders or syndromes including, e.g., the diseases and disorders disclosed above and/or other pathologies and disorders of the like. The method includes contacting a test compound with a Y136 polypeptide and determining if the test compound binds to said Y136 polypeptide. Binding of the test compound to the Y136 polypeptide indicates the test compound is a modulator of activity, or of latency or predisposition to the aforementioned disorders or syndromes.

Also within the scope of the invention is a method for screening for a modulator of activity, or of latency or predisposition to disorders or syndromes including, e.g., the diseases and disorders disclosed above and/or other pathologies and disorders of the like by administering a test compound to a test animal at increased risk for the aforementioned disorders or syndromes. The test animal expresses a recombinant polypeptide encoded by a Y136 nucleic acid. Expression or activity of Y136 polypeptide is then measured in the test animal, as is expression or activity of the protein in a control animal which recombinantly-expresses Y136 polypeptide and is not at increased risk for the disorder or syndrome. Next, the expression of Y136 polypeptide in both the test animal and the control animal is compared. A change in the activity of Y136 polypeptide in the test animal relative to the control animal indicates the test compound is a modulator of latency of the disorder or syndrome.

In still another aspect, the invention relates to methods for diagnosing a viral infection comprising the steps of assaying for the presence or absence of a Y136 protein in a biological sample. In one embodiment the invention comprises detecting the amount and/or presence of a Y136 protein in a test sample and comparing to a control. The presence and amount of Y136 protein correlates to a poxvirus infection.

In yet another aspect, the invention includes a method for determining the presence of or predisposition to a disease associated with altered levels of a Y136 polypeptide, a Y136 nucleic acid, or both, in a subject (e.g., a human subject). The method includes measuring the amount of the Y136 polypeptide in a test sample from the subject and comparing the amount of the polypeptide in the test sample to the amount of the Y136 polypeptide present in a control sample. An alteration in the level of the Y136 polypeptide in the test sample as compared to the control sample indicates the presence of or predisposition to a disease in the subject. Preferably, the predisposition includes, e.g., the diseases and disorders disclosed above and/or other pathologies and disorders of the like. Also, the expression levels of the new polypeptides of the invention can be used in a method to screen for various disorders as well as to determine the stage of particular disorders.

In yet another aspect, the invention can be used in a method to identity the cellular receptors and downstream effectors of the invention by any one of a number of techniques commonly employed in the art. These include but are not limited to the two-hybrid system, affinity purification, co-precipitation with antibodies or other specific-interacting molecules.

Pharmaceutical Forms

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid. Pharmaceutical compositions of the invention include therapeutically- or prophylactically-effective amounts of a therapeutic and a pharmaceutically-acceptable carrier. The therapeutic can be, e.g., a Y136 nucleic acid, for example, a peptide nucleic acid, a cDNA, or RNA, such as for example, a small inhibitory RNA; a Y136 polypeptide; or an antibody specific for a Y136 polypeptide. In a further aspect, the invention includes, in one or more containers, a therapeutically- or prophylactically-effective amount of this pharmaceutical composition.

As used herein, "therapeutically effective dose" refers to that amount of the therapeutic sufficient to result in amelioration or delay of symptoms. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A pharmacological composition or formulation refers to a composition or formulation in a form suitable for administration, e.g., systemic administration, into a cell or subject, preferably a human. By "systemic administration" is meant in vivo systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

The compounds, nucleic acid molecules, polypeptides, and antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In any aspect of the invention, the therapeutic composition of the invention can be in any pharmaceutically acceptable form and administered by any pharmaceutically acceptable route, for example, the therapeutic composition can be administered as an oral dosage, either single daily dose or unitary dosage form, for the treatment of a muscle damage due to a myocardial infarction, sclerotic lesion, or muscle tear due to sports-related activity to promote the regeneration and repair of the damaged muscle tissue. Such pharmaceutically acceptable carriers and excipients and methods of administration will be readily apparent to those of skill in the art.

By pharmaceutically acceptable formulation is meant, a composition or formulation that allows for the effective distribution of the nucleic acid molecules of the instant invention in the physical location most suitable for their desired activity. Non-limiting examples of agents suitable for formulation with the nucleic acid molecules of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly (DL-lactide-coglycolide) microspheres for sustained release delivery after implantation (Emerich, D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies, including CNS delivery of nucleic acid molecules include material described in Boado et al., 1998, J. Pharm. Sci., 87, 1308-1315; Tyler et al, 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058. All these references are hereby incorporated herein by reference.

Preparations for administration of the therapeutic of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

The invention also features the use of the composition comprising surface-modified liposomes containing poly (ethylene glycol) lipids (PEG-modified, or long-circulating liposomes or stealth liposomes). Nucleic acid molecules of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose or pharmaceutically effective amount is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the negatively charged polymer.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

The formulations can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such, as colloidal silicon dioxide; a sweetening agent such as sucrose or saccharin; or a flavoring agent such as peppermint, methyl salicylate, or orange flavoring.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR™, (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., the therapeutic complex of the invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The negatively charged polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and the other compositions known in the art.

Nucleic acid molecules of the invention can also be administered in the form of suppositories, e.g., for rectal administration of the drug or via a catheter directly to the bladder itself. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols. Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The amount of active ingredient that can be combined with the carrier materials to produce a single dosage form varies depending upon the host treated and the particular mode of administration. Dosage unit forms generally contain between from about 1 mg to about 1000 mg of an active ingredient.

It is understood that the specific dose level for any particular patient or subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water. The composition can also be administered to a subject in combination with other therapeutic compounds to increase the overall therapeutic effect. The use of multiple compounds to treat an indication can increase the beneficial effects while reducing the presence of side effects.

EXAMPLES

Type I and Type III IFNs, and their Cellular and Viral Receptors.

Subunits of IFN receptor complexes and receptors for IL-10-related cytokines comprise the class II cytokine receptor family (CRF2) (Kotenko, 2002; Kotenko et al, 2004; Langer et al, 2004). All these receptors share limited sequence similarity in their extracellular domains and common structural features. In contrast, VACV protein B18 belongs to the immunoglobulin family and reveals highest similarity to other poxvirus-encoded B18 orthologues, such as Variola virus (VARV) D9 and YLDV Y136 proteins (FIG. 1A). These viral proteins demonstrate most similarity to cellular receptors from the IL-1 receptor family (members of the immunoglobulin superfamily) (Sims, 2002; Dunne and O'neill, 2003), such as IL-1 receptor type II (IL-1R2) and IL-1 receptor-like 1 (IL-1RL1), and do not share significant similarity with the ligand binding subunits of the type I and type III IFN receptor complexes, IFN-αR2 and IFN-λR1, respectively (FIG. 1A). Nevertheless, the B18 protein binds and neutralizes IFN-α, IFN-ω and IFN-β (Colamonici et al, 1995; Symons et al, 1995; Liptakova et al, 1997).

Although the 13 human IFN-αs are very similar, other members of the type I IFN family demonstrate only limited similarity. For instance, the latest additions to the family, IFN-κ and IFN-ε, share less than 30% of aa identity with IFN-αs (FIG. 1B). The similarity between type I and type III IFNs is even lower and ranges from 15 to 20% aa identity. Therefore, based on simple sequence comparison of receptors and ligands, it is not possible to predict whether Y136 (or B18) would neutralize type I and type III IFNs.

Y136 Protein Inhibits Type I IFNs from Primates but not Rodents.

Initially we observed that the supernatant from owl monkey kidney (OMK) cells infected with YLDV contained an inhibitor of human IFN-α2 that was not present in the supernatant of mock-infected cells (data not shown). To determine if the Y136R gene encoded this activity, the gene was expressed from recombinant VACV vAA6 (Symons et al, 1995), a VACV strain from which the B18R gene encoding a type I IFN inhibitor had been deleted. The Y136 protein was expressed with or without a C-terminal HA tag and the recombinant viruses were called vY136 and vY136-HA. Immunoblotting showed that the supernatants of vY136-HA-infected cells expressed a secreted protein of about 80 kDa that was absent from controls (FIG. 2A). The size of the protein was greater than that of B18 (60-65 kDa) (Symons et al, 1995) because it contains 12 sites for attachment of N-linked carbohydrate compared to 5 sites in B18. Consistent with Y136 being glycosylated, its secretion from infected cells was blocked by the glycosylation inhibitor tunicamycin (data not shown).

To determine if Y136 would inhibit type I IFNs, different amounts of conditioned supernatant from VACV-infected cells were mixed with human IFN-α2 (FIG. 2B) or IFN-β (FIG. 2C) and the ability of the mixture to block plaque formation by Cocal virus was determined on HeLa cells. The Y136 protein, with or without a C-terminal HA tag, inhibited the anti-viral activity of both human IFNs. As expected the parental virus vAA6 and mock-infected cells did not express a secreted type I IFN inhibitor. Next we tested the activity of Y136 against rodent IFNs and found that Y136 was unable to inhibit mouse IFN-α (FIG. 2D), mouse IFN-β (FIG. 2E) or rat IFN-α (data not shown). In contrast, the VACV B18 protein inhibited mouse IFN-α but not IFN-β as reported previously (Symons et al, 1995; Smith and Alcami, 2002), indicating it has a broader species specificity. Y136 also inhibited rhesus monkey IFN-α (FIG. 2F) at least as well as did B18. Thus, Y136 is a soluble inhibitor of primate type I IFNs but did not inhibit rodent type I IFNs and this specificity is consistent with the fact that YLDV was derived from primates (for review see (Smith, 2006)).

Figure 3:
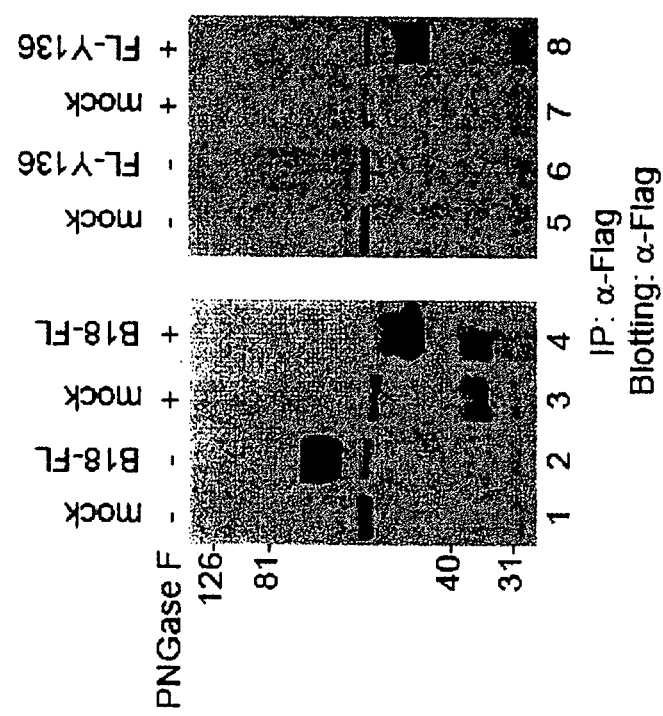

We then generated recombinant VACV B18 and YLDV Y136 proteins from uninfected mammalian cells to investigate comprehensively whether these viral proteins can block activity of various IFNs. The B18R and Y136R genes were cloned into mammalian expression vectors pEF-X-FL (Gallagher et al, 2000) and pEF-SPFL (Kotenko et al, 2000), resulting in plasmids pEF-B18-FL, pEF-Y136-FL, pEF-SPFL-B18 and pEF-SPFL-Y136, respectively. These vectors enable a FLAG epitope to be fused to the viral protein at either the C terminus (B18-FL and Y136-FL) or the N terminus (FL-B18 and FL-Y136). COS-1 cells were transfected with the plasmids and three days later conditioned media were collected and analyzed by immunoblotting (FIG. 3 and data not shown). Plasmids producing the highest levels of expression of secreted proteins, pEF-B18-FL and pEF-SPFL-Y136, were selected for further analyses and biological assays (FIGS. 4-8). Immunoblotting revealed that B18-FL and FL-Y136 were secreted from COS cells and migrated on the SDS-polyacrylamide gels as broad bands of about 60 to 65 kDa and 70 to 80 kDa, respectively (FIG. 3). These results are in accord with previously published data for B18 protein (Symons et al, 1995) and with results observed for Y136 secreted from vY136-HA-infected cells (FIG. 2A). Treatment with peptide N-glycosidase F (PNGase F) reduced the apparent molecular masses of these proteins to about 50 kDa for B18 and 45 kDa for Y136, confirming they are glycosylated. Indeed, there are five and twelve potential sites for N-linked glycosylation (N-X(except P)-T/S) in B18 and Y136 proteins, respectively.

IFN-κ and IFN-ε Signal Through Canonical Type I IFN Receptor Complex.

To characterize IL-10, IL-22 and IFN-λ receptor complexes, we had created a series of reporter hamster cell lines that respond to these human cytokines specifically (Kotenko et al, 1997; Kotenko et al, 2001a; Kotenko et al, 2003). Cytokines demonstrate various degrees of species specificity. Hamster cells are not responsive to human IFNs and IL-10-related cytokines (FIG. 4 and (Soh et al, 1994; Kotenko et al, 2003)). Therefore, appropriate human receptor subunits must be expressed in hamster cells to render them responsive to a given human cytokine. One receptor subunit in each receptor complex determines signal transduction specificity (Kotenko and Pestka, 2000; Kotenko, 2002). When the natural intracellular domain of a signaling receptor subunit is replaced by the IFN-γR1 intracellular domain in a reconstituted functional receptor complex for a particular cytokine, this cytokine induces IFN-γ-like signaling and biological activities that can be uniformly measured. This approach allowed us to generate hamster cell lines that signal specifically in response to a single human cytokine and to more easily monitor signaling of cytokines, such as IFN-λs, which induce weak signaling in intact cells due to the low level of receptor expression.

Therefore, to detect signaling in response to either type I or type III human IFNs, we utilized hamster cells expressing human IFN-λR1/IFN-γR1 (λR1/γR1) and IL-10R2 chains (Kotenko et al, 2003) (FIG. 4A), and created hamster cells responsive to human type I IFNs. These hamster cells express human chimeric IFN-αR2/IFN-γR1 (αR2/γR1) and IFN-αR1/IFN-γR2 (αR1/γR2) receptor chains that were generated by replacing the intracellular and transmembrane domains of IFN-αR2 and IFN-αR1 chains by the corresponding domains of IFN-γR1 and IFN-γR2 chains, respectively (FIG. 4A). Hamster cells expressing modified human type I and type III IFN receptor complexes were designated αR/γR and λR/γR cells, respectively. The ability of these cells to respond to various type I and type III IFNs was tested by measuring cytokine-induced STAT1 activation in electrophoretic mobility shift assay (EMSA).

Parental hamster cells were unresponsive to either type I or type III human IFNs (FIG. 4B). All type III IFNs were able to activate STAT1 only in λR/γR cells and not in αR/γR cells (FIG. 4B and data not shown), confirming that type III IFNs signal through a unique receptor complex composed of IFN-λR1 and IL-10R2 and do not cross-react with the type I IFN receptor complex. To obtain human IFN-β, IFN-ω, IFN-κ and IFN-ε, their genes were amplified by PCR from genomic DNA, cloned into the mammalian expression vector pcDEF3 (Goldman et al, 1996) (pEF) and expressed in COS-1 cells. The relative amounts of IFNs in COS cell conditioned media were determined in IFN-α-equivalent units per ml based on antiviral assays (FIG. 5B and data not shown) in comparison with antiviral potency of recombinant E. coil-produced IFN-α2 in similar assays. IFN-α-equivalent units, determined in antiviral assays, correlated very well with STAT1-inducing ability of various IFNs in EMSA (FIG. 5B and data not shown). Recombinant IFN-α2 and COS cell-produced IFN-β, IFN-ω, IFN-κ and IFN-ε were used to demonstrate that all type I IFNs, including IFN-κ and IFN-ε, signal through the canonical type I IFN receptor complex composed of IFN-αR1 and IFN-αR2. None of the type I IFNs was able to induce signaling through the type III IFN receptor complex (FIG. 5B). This is the first demonstration that the recently identified IFN-κ and IFN-ε signal through the same receptor complex as all the other type I IFNs.

VACV B18 is a Specific Antagonist of all Human Type I IFNs and not Type III IFNs.

We used λR/γR and αR/γR reporter cell lines to evaluate whether B18 protein can inhibit signaling induced by either all type I IFNs, including IFN-κ and IFN-ε, or type III IFNs. The λR/γR and αR/γR cells were treated by IFN-λs, and IFN-α2, IFN-β, IFN-ω, IFN-κ and IFN-ε, respectively, with or without B18 protein (FIG. 5A). We found that B18 blocked the ability of all type I IFNs to induce STAT1 activation in αR/γR cells. In contrast, type III IFN signaling was not affected by B18 protein. Therefore, B18 inhibited signaling induced by all human type I IFNs, but not by type III IFNs (FIG. 5A).

Next we determined whether B18 can inhibit the antiviral activities of a broad range of IFNs on colorectal adenocarcinoma (HT-29) cells that respond to both type I and type III IFNs (Kotenko et al, 2003). The ability of various IFNs to protect HT-29 cells against infection by Vesicular stomatitis virus (VSV) was measured in the presence or absence of B18 (FIG. 5B) as the reduction of virus-mediated cytopathic effect (CPE). The antiviral activity of all type I IFNs was inhibited strongly by B18. In the presence of B18 much higher amounts of type I IFNs were required to overcome the neutralizing effect of B18 and achieve 50% protection of the cells from CPE (FIG. 5B). Noticeably, B18 had different neutralizing activity against different type I IFNs. It had greatest neutralizing ability toward IFN-β, which is the earliest IFN produced by cells in response to viral infection (Levy et al, 2001; Honda et al, 2005). We also found that type III IFNs were not affected by B18 (FIG. 5B).

The effect of B18 on IFN activity was also examined by measurement of IFN-mediated induction of MHC class I antigen expression on HT-29 cells by flow cytometry. The up-regulation of MHC class I antigen expression in response to type I but not type III IFNs was reduced by B18 (FIG. 5C). In most cases the level of MHC class I antigen expression was reduced to the basal level by B18 (FIG. 5C).

Y136 Neutralizes Signaling and Biological Activities of Both Type I and Type III IFNs.

Considering the limited similarity between B18 and Y136 (27% aa identity), we performed a similar series of experiments with Y136. As shown in FIG. 6A, Y136 completely neutralized the ability of both type I and type III IFNs to activate STAT1 in reporter cell lines. In agreement with its ability to block IFN signaling, Y136 also inhibited biological activities induced by both type I (FIG. 2) and type III IFNs. Y136 blocked antiviral protection and up-regulation of MHC class I antigen expression in HT-29 cells in response to both type I and type III IFNs (FIGS. 6B and C).

Because type III IFNs reveal a similar degree of aa identity to both type I IFNs and IL-10-related cytokines, we investigated whether viral receptors crossreact with IL-10-related cytokines. With the use of 10R/γR and 22R/γR reporter cell lines that respond to human IL-10 and IL-22, respectively (Kotenko et al, 1997; Kotenko et al, 2001a), we demonstrated that Y136 and B18 did not inhibit IL-10 or IL-22 signaling (FIG. 6D). Neither viral protein suppressed IFN-γ signaling in HT-29 cells (FIG. 6D).

Type I and Type III IFNs Compete for Binding to Y136.

Next we characterized the interaction of IFNs with B18 and Y136 by covalent crosslinking (FIGS. 7A and B). Radiolabeled IFN-α2-P (Li et al, 1989) and His-Strep-IFN-λ1-P were crosslinked to either B18 or Y136 in solution with or without an excess of unlabeled (cold) IFNs as competitors, and the crosslinked complexes were analyzed by SDS-PAGE. The major radiolabeled bands of ~20 kDa (FIG. 7A) and ~45 kDa (FIG. 7B) correspond to free IFN-α2-P and His-Strep-IFN-λ1-P, respectively. These bands did not change upon crosslinking demonstrating that IFN-α2 and IFN-λ1 are monomers in solution. Crosslinking of radiolabeled IFN-α2-P to B18 resulted in the appearance of additional complexes of ~70 to 90 kDa (FIG. 7A), whereas the presence of B18R protein did not change the pattern of crosslinking of radiolabeled His-Strep-IFN-λ1-P (FIG. 7B). Addition of excess cold type I IFN, but not type III IFN, competed with radiolabeled IFN-α2-P for binding to B18 demonstrating the specificity of the interaction (FIG. 7A).

In contrast, the incubation of Y136 with either [$^{32}$P]-IFN-α2-P or [$^{32}$P]-His-Strep-IFN-λ1-P followed by covalent crosslinking resulted in formation of complexes of ~100 to 160 kDa for [$^{32}$P]-IFN-α2-P (FIG. 7A) and ~130 to 190 kDa for [$^{32}$P]-His-Strep-IFN-λ1-P (FIG. 7B). Interestingly, an excess of either unlabeled type I or type III IFN inhibited formation of these complexes, confirming that Y136 binds both type I and type III IFNs and demonstrating that they interact with the same ligand-binding site on Y136 (FIGS. 7A and B).

Similarly, immunoprecipitation of complexes containing viral receptors and radiolabeled IFN-α with FLAG antibody demonstrated that all type I IFNs and not type III IFNs competed with IFN-α for binding to B18-FL (FIG. 7C). In contrast, both type I and type III IFNs competed with IFN-α for binding to FL-Y136 protein (FIG. 7D). Significantly, B18 also competed with FL-Y136 for binding with radiolabeled IFN-α (FIG. 7D).

Competition of ligands and receptors for the binding sites was also demonstrated by EMSA (FIG. 8A). An excess of IFN-α sequestered FL-Y136 and consequently restored signaling by type III IFNs in λR/γR cells. Similarly, an excess of IFN-λ1 bound FL-Y136 and thereby inhibited its ability to neutralize IFN-α and IFN-β signaling in αR/γR cells. However, an excess of IFN-λ1 did not prevent B18-FL inhibiting IFN-α signaling in αR/γR cells.

Because B18 is present on the cell surface and in solution (Morikawa and Ueda, 1993; Alcami et al, 2000), we investigated whether COS cells expressing B18 or Y136 retain biologically active proteins on the cell surface (FIGS. 8B and C). These cells were washed to remove soluble IFN-binding proteins, and then incubated with IFN-β. The medium was then harvested and used in EMSA with reporter cell lines to determine whether the COS cells had removed IFN-β from the supernatant. If IFN-β was still present in the medium it would induce STAT1 activation. Parental untreated COS cells were used as a control. As shown in FIGS. 8B and C, COS cells expressing B18 or Y136 sequestered IFN-β from the medium, whereas parental COS cells did not. These experiments demonstrated that some B18 and Y136 is retained on the cell surface whereas some is also secreted.

We also generated HT-29 cells constitutively expressing either B18 or Y136. Noticeably, the basal level of MHC class I antigen expression in these cells was down-regulated in comparison with those in parental cells suggesting that a low level of type I IFN signaling was maintained in HT-29 cells (FIG. 8D). In agreement with all previous experiments, HT-29 cells expressing B18 protein did not respond to type I IFNs while retaining type III IFN responsiveness. In contrast, HT-29 cells expressing Y136 did not respond to either type I or type III IFNs, as evaluated by the ability of IFNs to up-regulate MHC class I antigen expression in these cells.

We and others recently discovered type III IFNs, denoted IFN-λ1, IFN-λ2 and IFN-λ3, also known as interleukin (IL)-29 and IL-28A and IL-28B. They signal through an IFN-λ receptor complex composed of a unique IFN-δR1 chain and a shared IL-10R2 chain that is also the second subunit of the IL-10, IL-22 and IL-26 receptor complexes (FIG. 9).

Although three types of IFNs signal through distinct receptor complexes, all IFN receptor subunits demonstrate limited amino acid (aa) similarity in their extracellular domains and belong to the class II cytokine receptor family (CRF2). All IFNs activate Janus kinase (JAK)-Signal Transducers and Activators of Transcription (STAT) signal transduction pathway. The activation of type I and type III IFN receptors, despite their differences, results in similar signaling events including phosphorylation of Jak kinases Jak1 and Tyk2 and phosphorylation of STAT1 and STAT2, as well as STAT3, STAT4 and STAT5 to a lesser extent (FIG. 9). STATs homo- or hetero-dimerize, translocate into the nucleus and bind to the promoter region of IFN-stimulated genes (ISGs) leading to gene transcription. STAT homo- and heterodimers bind to specific DNA elements. For instance, STAT1-STAT2 heterodimers associate with a DNA-binding protein IRF9 (p48) forming a transcriptional complex designated ISGF3 (IFN-stimulated gene factor 3), which binds to the IFN-stimulated response element (ISRE). Type II IFN activates predominately STAT1 and transcription of genes preceded by a GAS (γ-activated sequence) element.

The pattern of expression of type I and type III IFNs is very similar. Both types of IFNs are co-produced by a wide variety of nucleated cells in response to various viral infections and some other stimuli (LPS, poly I:C, bacterial/viral DNA). Treatment with diverse Toll-like receptor (TLR) agonists induces expression of the IFN-α/β and IFN-λ genes in monocyte-derived dendritic cells (MDDCs) and plasmacytoid dendritic cells (PDCs). Importantly, CpG DNA, which signals via TLR9 and has been a implicated in the pathogenesis of SLE, induced coexpression of IFN-α, IFN-β, and IFN-λ in PDCs (FIG. 9). The similar pattern of expression of type I and type III IFNs is consistent with the existence of several common regulatory elements in promoters of the IFN-8 and type I IFN genes and with the involvement of similar signaling mediators and transcriptional factors in the regulation of gene expression of type I and type III IFNs.

Binding of IFNs to their corresponding cellular receptor complexes induces similar downstream signaling events and, consequently, biological activities including the ability to induce an antiviral state in cells. However, whereas type I IFN receptors are expressed in most cell types, IFN-δR1 demonstrates a more restricted pattern of expression, limiting response to type III IFNs to primarily epithelial-like tissues, B cells and activated DCs and pDCs. Microarray analysis demonstrated that both types of IFNs induced nearly identical sets of genes in responsive cells. Many ISGs encode important antiviral mediators that suppress virus replication through a variety of well-orchestrated and diverse mechanisms, making the IFN system one of the most important defense mechanisms against viral infections.

Figure 10A:
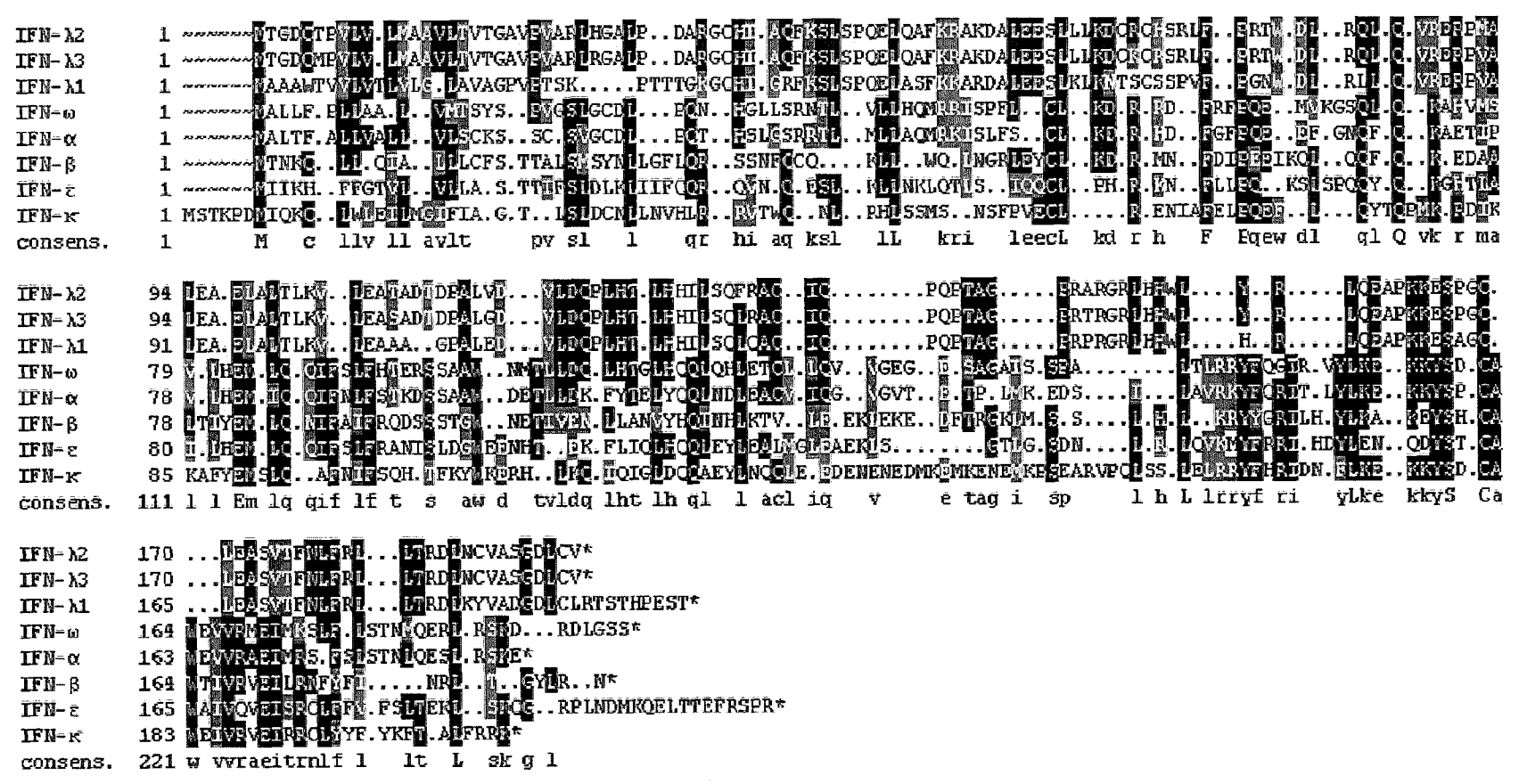
Figure 10B:
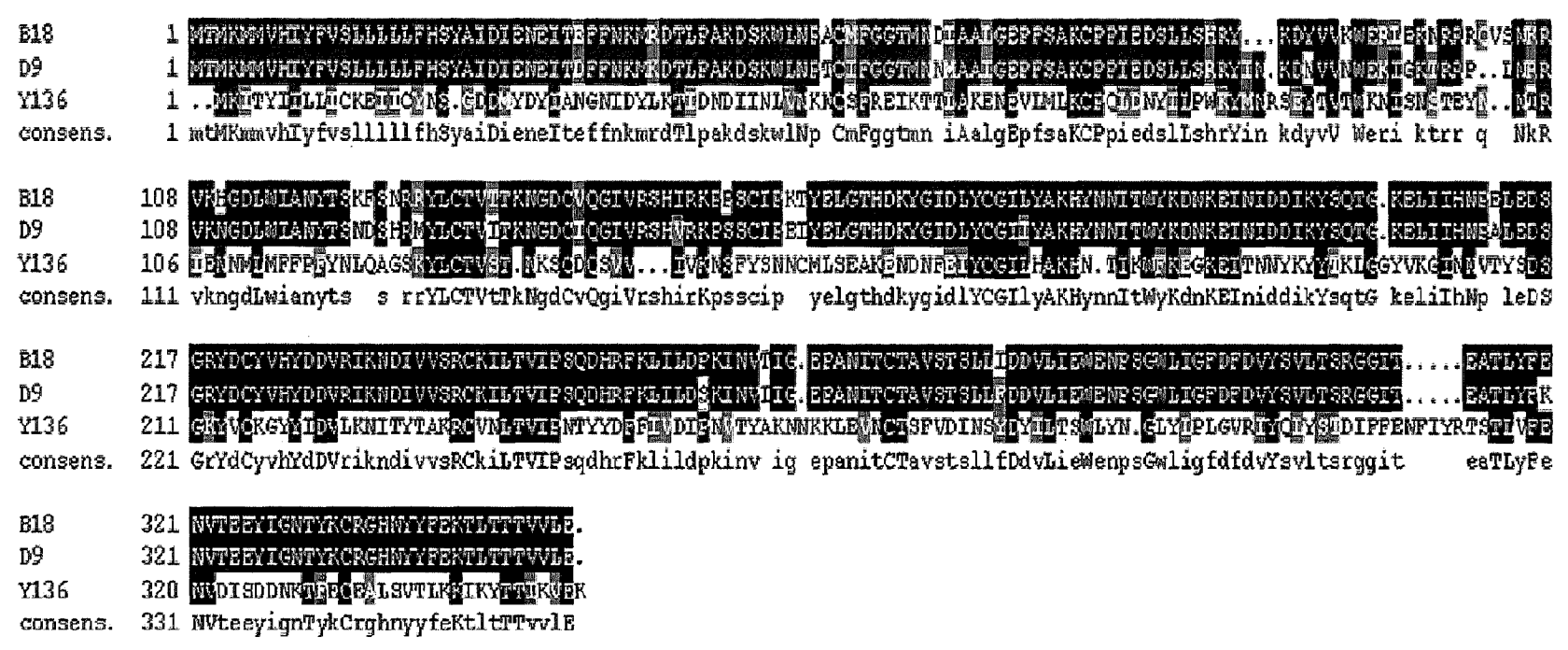

In turn, viruses have developed many strategies to circumvent IFN-induced antiviral protection, generally interfering with IFN signaling. The Poxyiridae are a family of large dsDNA viruses that encode numerous immunomodulatory proteins. Vaccinia virus (VACV), the smallpox vaccine, encodes two secreted proteins that function as IFN antagonists. The B8 protein is the soluble receptor for IFN-γ, whereas the B18 protein of VACV strain Western Reserve binds IFN-α, IFN-β and IFN-ω and suppresses interaction of IFNs with their membrane-bound receptor complexes. Many orthopoxviruses encode orthologues of B18 that are predicted to, or have been shown to, neutralize IFN-α/β. For example, Yaba-like disease virus (YLDV), a strain of Tanapoxvirus, which causes vesicular skin lesions in primates and can be transmitted to humans, encodes protein Y136 that shares 27% aa identity with B18 (FIG. 10A). However, the ability of Y136 to inhibit biological activities of IFNs is unknown. Similarly, the ability of poxvirus IFN-binding proteins to neutralize type III IFNs and novel members of the type I IFN family, IFN-κ and IFN-ε has not been investigated hitherto. Although the 13 human IFN-α's are very similar, other members of the type I IFN family demonstrate only limited similarity (IFN-κ and IFN-ε share less than 30% of aa identity with IFN-α's; FIG. 10B). Type I and type III IFNs have even lower sequence identity (15 to 20%; FIG. 10B), utilize distinct receptor complexes, and do not demonstrate any receptor binding cross-reactivity. Therefore, it is mystifying that Y136 protein interacts with both types of IFNs in a competitive manner.

It is interesting that cellular type I and type III IFN receptors belong to CRF2 receptor family, while the viral IFN-binding proteins belong to the IL-1 receptor family and these families do not reveal any substantial primary sequence similarity (FIG. 10A). All cellular IFN receptors as well as receptors for IL-10-related cytokines form the class II cytokine receptor family and have fibronectin like domains. In contrast, both B18 and Y136 belong to the immunoglobulin family and reveal highest similarity to other poxvirus-encoded B18 orthologues, such as Variola virus (VARV) D9 (FIG. 10A), and demonstrate most similarity to cellular receptors from the IL-1 receptor family (part of the immunoglobulin superfamily), particularly to IL-1 receptor type II (IL1R2; a decoy receptor that binds IL-1α/β) and IL-1 receptor-like 1 (IL1RL1; a ligand-binding chain of the IL-33 receptor complex). Both receptors are membrane-bound proteins. However, the IL1RL1 gene has a naturally occurring splice variant that generates a soluble IL1RL1s protein. Therefore, this protein can be utilized to generate "humanized" IFN antagonists. Although the structure of IL1RL1s has not been determined, crystal structures of the IL-1 receptor (IL1R1) with either IL-1β or IL-1 receptor antagonist (IL1RA) were solved. The crystal structure shows that sIL1R1 consists of three immunoglobulin-like (Ig-1) domains that can be well aligned with IL1RL1 and IFN antagonists (FIG. 10C). Each Ig-1 domain consists of 7 to 9β sheets. Therefore, the immunoglobulin-like domains of IL1RL1 can be swapped with those of B18 and Y136 to create IL1RL1/B18(Y136) chimeras.

Chimeric IL1RL1/B18(Y136) proteins can be created as briefly outlined in FIG. 11 and described here. IL1RL1s is induced by proinflammatory stimuli in various cells. Therefore, IL1RL1s cDNA can be amplified by RT-PCR from phorbol 12-myristate 13-acetate (PMA)-treated human peripheral blood mononuclear cells (this mRNA as well as several cDNA libraries are available in the lab) and, similar to genes encoding viral proteins, cloned into mammalian expression vector, which will enable a FLAG epitope to be fused to IL1RL1s at the N terminus (FL-IL1RL1s). The resulting expression plasmid (pEF-SPFL-IL1RL1s) can be transiently transfected into COS cells, and the presence of FL-IL1RL1s in conditioned media will be evaluated by immunoblotting with FLAG Ab as described. Thus, expression plasmids, with identical backbone and flanking sites, encoding either FLIL1RL1s, FL-Y136, or FL-B18 can be created (See, for example, FIG. 11). Next with the use of mutagenesis and/or PCR we can introduce two unique restriction sites into all the genes; one site can be introduced between first D1 and second D2 Ig-1 domains, second site can be introduced between second D2 and third D3 Ig-1 domains (FIG. 11). This allows for easy swapping of Ig-1 domains between proteins to create (PMA)-treated human peripheral blood mononuclear cells (this mRNA as well as several cDNA libraries are available in the lab) and, similar to genes encoding viral proteins, cloned into mammalian expression vector, which will enable a FLAG epitope to be fused to IL1RL1s at the N terminus (FL-IL1RL1s). The resulting expression plasmid (pEF-SPFL-IL1RL1s) can be transiently transfected into COS cells, and the presence of FL-IL1RL1s in conditioned media will be evaluated by immunoblotting with FLAG Ab as described. Thus, expression plasmids, with identical backbone and flanking sites, encoding either FLIL1RL1s, FL-Y136, or FL-B18 can be created (See, for example, FIG. 11). Next with the use of mutagenesis and/or PCR we can introduce two unique restriction sites into all the genes; one site can be introduced between first D1 and second D2 Ig-1 domains, second site can be introduced between second D2 and third D3 Ig-1 domains (FIG. 11). This allows for easy swapping of Ig-1 domains between proteins to create all possible combinations of Ig-1 domains as shown in the example schematic for IL1RL1/Y136 chimeras (FIG. 11). Similar chimeras can be generated for IL1RL1/B18.

Chimeric proteins capable of inhibiting IFNs are selected and further modified by exchanging β sheets and/or specific aa in Ig-1 domains that demonstrated involvement in IFN binding. For example, regions can be selected that are likely being conserved to maintain structure and/or functions of viral IFN antagonists. For example, higher conservation of identical aa can be observed in second halves of D1 and D2 Ig-1 domains than in first halves of the domains (FIG. 10C). These regions may participate in binding of IFN molecules, and aa from these regions will be grafted by mutagenesis into an appropriate chimeric molecule.

Exemplary Methods

Plasmid construction. To clone gene B18R a PCR was performed with either primers 5'-ATGGTACCGATGAC-GATGAAAATGATGGTAC-3' (B18R-1; SEQ ID NO. 7) and 5'-GTAGCTAGCCTCCAATACTACTGTAGT-3' (B18R-3; SEQ ID NO. 9), or 5'-TTGGATCCCCACAGTTACGC-CATAGACAT-3' (B18R-4; SEQ ID NO. 10) and 5'-CAT-TCTAGATTTACTCCAATACTACTGTAG-3' (B18R-2; SEQ ID NO. 8), and with a plasmid encoding the B18R gene from VACV strain Western Reserve (WR) as template. The PCR products were cloned into either plasmid pEF-X-FL (Gallagher et al, 2000) or pEF-SPFL (Kotenko et al, 2000) with the use of KpnI and NheI, or BamHI and XbaI restriction endonucleases, resulting in plasmids pEF-B18R-FL and pEF-SPFL-B18R, respectively. Similarly, the 136R gene was amplified by PCR with either primers 5'-TAGGTACCAT-GAAAATCACATATATAATAC-3' (136R-1; SEQ ID NO. 11) and 5% TTTGCTAGCTTTTTCTACTTTAATGGTTG-3' (136R-3; SEQ ID NO. 13), or 5'-CTCGGATCCCAAT-AGCGGCGATGATATG-3' (136R-4; SEQ ID NO. 14) and 5'-TTGAATTCATTTTTCTACTTTAATGGTTGTA-3' (136R-2; SEQ ID NO. 12), and with a plasmid containing gene Y136R (Lee et al, 2001) as template. The PCR products were cloned into either plasmid pEF-X-FL or pEF-SPFL with the use of Kpn I and NheI, or BamHI and EcoRI restriction endonucleases, resulting in plasmids pEF-Y136-FL and pEF-SPFL-Y136, respectively.

Human genomic DNA and primers 5'-TTGGTACCAT-GACCAACAAGTGTCTCCTCC-3' (beta-1; SEQ ID NO. 15) and 5'-AGGAATTCAGTTTCGGAGGTAACCTG-TAAG-3' (beta-2; SEQ ID NO. 16), '-TCAGGTACCAATG-GCCCTCCTGTTCCCTC-3' (omega-1; SEQ ID NO. 17) and 5'-ATGAATTCAAGATGAGCCCAGGTCTCTA-3' (omega-2; SEQ ID NO. 18), '-AAAGGTACCATGAT-TCAAAAGTGTTTGTGGCTTG-3' (kappa-2; SEQ ID NO. 19) and 5'-CCGAATTCATTTCCTCCTGAATAGAGCT-GTAA-3' (kappa-4; SEQ ID NO. 20), and 5'-CCGGTAC-CATGATTATCAAGCACTTCTTTGG-3' (ifn-new-3; SEQ ID NO. 21) and 5'-CCGAATTCCTACCTCGGGCT-TCTAAACTCTGTAG-3' (inf-new-4; SEQ ID NO. 22) were used for PCR to amplify IFN-β, IFN-ω, IFN-κ and IFN-ε genes and clone them into pcDEF3 expression vector (Goldman et al, 1996), resulting in plasmids pEF-IFN-β and pEF-IFN-ω, pEF-IFN-κ and pEF-IFN-κ, respectively.

Plasmid pEF-His-Strep-IFN-λ1-P encodes secreted human IFN-λ1 tagged at its N terminus with the His-Strep tag (HHHHHHPDHWSHPQFEK; SEQ ID NO. 23) and at its C terminus with the Arg-Arg-Ala-Ser-Val-Ala sequence, the consensus amino acid sequence recognizable by the catalytic subunit of the cAMP-dependent protein kinase, allowing the IFN-λ1 protein to be phosphorylated. The tags were introduced by PCR with appropriate primers.

Fragments encoding the extracellular domains of IFN-αR1 and IFN-αR2 were amplified by PCR with T7 primer and either 5'-ATCGCTAGCCATTTAGAGGTATTTCCTGG-3' (αR1EC; SEQ ID NO. 24) or 5'-ATCGCTAGCCATTTG-GCAGATTCTGCTGA-3' (αR2EC; SEQ ID NO. 25) primer, and pαR1 or pαR2 plasmid (Kotenko et al, 1996) as a template. The PCR fragments were cloned into KpnI and NheI restriction sites of either pEF3-FL-γR2/γR2 (Kotenko et al, 1999) or pEF2λR1/R1 plasmid (Kotenko et al, 2003), resulting in plasmids pEF-IFN-αR1/IFN-R2 (pEF-αR1/γR2) and pEF-IFN-αR2/IFN-R1 (pEF-αR2/γR1), respectively.

To ensure that both receptors are expressed in a single transfected cell, tandem vectors encoding two receptors, αR2/γR1 and αR1/γR2, in which the expression of each receptor is controlled by separate promoters and polyadenylation signals, were constructed as follows. The fragment containing the EF-1 promoter, the αR2/γR1 coding sequence, and the bovine growth hormone (BGH) polyadenylation signal was released from plasmid pEF-αR2/γR1 by digestion with BsaI and BssHII restriction endonucleases and ligated into the BsaI and MluI sites of the pEF-αR1/γR2 plasmid, resulting in plasmid pEF-αR2/R1+αR1/R2.

The nucleotide sequences of the modified regions of all constructs were verified in their entirety by DNA sequencing.

Construction of Recombinant VACVs Expressing Y136.

The Y136R gene was cloned into the thymidine kinase (TK) locus of the VACV strain vAA6 (strain WR with deleted B18R gene, (Symons et al, 1995)) downstream of the VACV p7.5K promoter. The Y136R gene was amplified by PCR using YLDV genomic DNA as template and primers forward 5'-ATTGGGATCCTAAACAATGAAAATCA-CATATATAATAC-3'(SEQ ID NO. 26) and reverse 5'-TAA-CAAGCTTCATTATTTTTCTACTTTAATGGTTG-3' (SEQ ID NO. 27). The PCR product was digested with BamHI and HindIII and cloned into plasmid pGS61 digested with the same enzymes (Smith et al, 1987) to place the Y136R gene downstream of the VACV 7.5K promoter within the TK gene. The resultant plasmid was called pGS61-Y136R. A similar plasmid (pGS61-Y136R-HA) was constructed in which the Y136R gene was fused at the C terminus to DNA encoding an influenza virus haemagglutinin (HA) epitope. Each plasmid was transfected into CV-1 cells that had been infected with vAA6 and recombinant VACVs were selected on human TK-143 cells in the presence of bromo-deoxyuridine as described previously (Smith et al, 1987). These viruses were called vY136 and vY136-HA.

Cells, Transfection and Flow Cytometry.

The 16-9 hamster-human somatic cell hybrid line, the Chinese hamster ovary cell (CHO-K1) hybrid containing a translocation of the long arm of human Chromosome 6 encoding the human IFNGR1 (Hu-IFN-R1) gene and a transfected human HLA-B7 gene (Soh et al, 1993), was from Sidney Pestka (UMDNJ). The cells were maintained in Ham's F12 cell culture medium (Sigma, St. Louis, Mo.) containing 10% heat-inactivated fetal bovine serum (FBS; Sigma). COS-1 cells, SV40 transformed fibroblast-like simian CV-1 cells, were maintained in DMEM medium (Sigma) with 10% FBS. Colorectal adenocarcinoma HT-29 cells were maintained in RPMI medium (Sigma) with 10% FBS. COS-1 cells were transfected as described previously (Kotenko et al, 2000). COS cell conditioned media (supernatants) were collected at 72 h and used as a source of the expressed proteins. The 16-9 cells and HT-29 cells were transfected with the use of TransIT-LT1 Transfection reagent (Minis Corp., Madison, WT). G418-resistant cells were selected in medium containing 450 ng/ml of G418.

To detect changes in MHC class I antigen (HLA-B7) expression, cells were treated with IFNs as indicated in the text and their MHC class I antigen expression was analyzed by flow cytometry. Cell surface expression of the HLA-B7 antigen was detected by treatment with the mouse W6/32 HLA monoclonal antibody (Barnstable et al, 1978), followed by fluorescein isothiocyanate-conjugated goat anti-mouse IgG (Jacksonackson ImmunoResearch Laboratories Inc., West Grove, Pa.).

Immunoprecipitation and Immunoblotting.

COS cell supernatants (1 ml) were incubated with FLAG M2 monoclonal antibody (mAb) (1 µg; Sigma) and protein A/G PLUS-Agarose beads (12 µl; Santa Cruz Biotechnology, Santa Cruz, Calif.) at 4° C. for 16 h. After incubation, beads were washed three times in ice-cold PBS, and precipitated proteins were separated by SDS-PAGE, transferred to a nitrocellulose membrane (Bio-Rad Laboratories, Hercules, Calif.), and analyzed by immunoblotting with FLAG mAb. Where indicated, immunoprecipitates were treated with N-Glycosidase (PNGase F, 1 µl; New England BioLabs, Beverly, Mass.) according to manufacturer's protocols.

Similarly, the supernatants of BS-C-1 cells infected with the indicated VACVs at 5 plaque-forming units (pfu)/cell for 18 h were collected and analyzed by SDS-PAGE and immunoblotting with HA mAb as described previously (Chen et al, 2006).

Electrophoretic Mobility Shift Assays (EMSAs).

To detect STAT1 activation, cells were treated with COS cell supernatants or purified recombinant proteins (IFN-α2, IFN-γ, IL-10 and IL-22; PeproTech, Rocky Hill, N.J.) for 15 min at 37° C. and used for EMSAs with a 22-bp DNA probe, containing the STAT1 binding site corresponding to the GAS element, as described previously (Kotenko et al, 1995). For neutralizing experiments, IFNs were preincubated with B18 or Y136 for 1 h at 22° C.

ELISA Assay.

An agent for detecting an analyte protein is an antibody capable of binding to an analyte protein, preferably an antibody with a detectable label. Antibodies can be polyclonal, or more preferably, monoclonal. An intact antibody, or a fragment thereof (e.g., Fab or F(ab)2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitation, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Thory of Enzyme Immunoassays", P. Tijssen, Elsevier Science Publishers, Amsterdam, 1985. Furthermore, in vivo techniques for detection of an analyte protein include introducing into a subject a labeled anti-an analyte protein antibody. For example, the antibody can be labeled with a radioactive marker whose presence and location in a subject can be detected by standard imaging techniques intracavity, or transdermally, alone or with effector cells.

Virus Infection, Antiviral Protection and IFN Inhibition Assays.

Antiviral assays were performed essentially as described (Familletti et al, 1981). An equal number of HT-29 cells was plated in 60 wells in the middle of 96-well microtiter plates and treated with two-fold serial dilutions of test IFNs for 24 h. COS cell conditioned medium containing B18 or Y136 proteins (50 μl in total volume of 250 μl/well) were used in selected wells. 24 h later the cells were challenged with VSV (a rhabdovirus, Indiana strain) and incubated further until controls showed full killing by virus (1-2 days). Cells not killed were visualized by staining with crystal violet.

BS-C-1 cells were mock-infected or infected at 5 pfu/cell with VACV strain vAA6, vY136, or vY136-HA for 24 h. The supernatants were collected and virions were removed by centrifugation (13,000 rpm, Beckman SW28, 90 mins, 4° C.) and filtration of the resulting supernatants through a 0.1 μm filter. The filtrate was then tested for inhibition of various IFNs using Cocal virus plaque formation assay as described previously (Symons et al, 1995). Data are expressed as the percentage inhibition of the antiviral effect of IFN on plaque formation by Cocal virus. Human IFN-β (PeproTech) was assayed on HeLa cells and rhesus monkey IFN-α was assayed on BS-C-1 cells. Mouse IFN-α, mouse IFN-β and rat IFN-α was assayed on mouse L929 cells.

Crosslinking.

IFN-α2-P was created as described (Li et al, 1989). His-Strep-IFN-λ1-P was expressed in COS cells and purified from the conditioned medium by affinity chromatography with Strep-Tactin columns according to the manufacturer's protocols (IBA GmbH, Gottingen, Germany). The proteins were labeled with [$^{32}$P]ATP and used for crosslinking as reported previously (Kotenko et al, 1995; Pestka et al, 1999; Kotenko et al, 2001b).

Data Analysis.

Programs PILEUP (Genetics Computer Group (GCG), Version 9.1), CLUSTAL X were used to align amino acid sequences of IFNs or their receptors, and to generate phylogenetic trees.

Additional objects and advantages of the present invention will be appreciated by one of ordinary skill in the art in light of the current description and examples of the preferred embodiments, and are expressly included within the scope of the present invention.

The invention claimed is:

1. A pharmaceutical composition comprising an isolated viral polypeptide of SEQ ID NO:1 having interferon (IFN) I and IFN III antagonist activity; and at least one of a pharmaceutically acceptable carrier, excipient, or adjuvant.

2. The pharmaceutical composition of claim 1, wherein the polypeptide comprises a fusion protein.

3. The pharmaceutical composition of claim 2, wherein the fusion protein comprises a polypeptide of SEQ ID NO:1 and a polypeptide of SEQ ID NO:5.

4. A method for inhibiting the activity of an interferon comprising administering to a subject in need thereof the pharmaceutical composition of claim 1 so that the activity of an interferon is inhibited.

5. The method of claim 4, wherein the interferon is at least one of a type I interferon, a type III interferon or a combination of both.

6. The method of claim 4, wherein the subject has symptoms associated with an immunological condition.

7. The method of claim 6, wherein the immunological condition is selected from the group of an autoimmune disease, systemic lupus erythematosus (SLE), acute allograft rejection, septic shock, and viral infection.

* * * * *